US011047850B2

(12) United States Patent
Jansen et al.

(10) Patent No.: US 11,047,850 B2
(45) Date of Patent: Jun. 29, 2021

(54) COMPOSITION FOR STABILIZATION OF ANTIBODY FORMULATIONS CONTAINING PERCP

(71) Applicant: Agilent Technologies, Inc., Santa Clara, CA (US)

(72) Inventors: Anna Mai Jansen, Valby (DK); Tina Brink Jakobsen, Ballerup (DK); Jesper Kuhnau, Alleroed (DK)

(73) Assignee: AGILENT TECHNOLOGIES, INC., Santa Clara, CA (US)

( * ) Notice: Subject to any disclaimer, the term of this patent is extended or adjusted under 35 U.S.C. 154(b) by 34 days.

(21) Appl. No.: 16/111,660

(22) Filed: Aug. 24, 2018

(65) Prior Publication Data

US 2019/0064155 A1    Feb. 28, 2019

Related U.S. Application Data

(60) Provisional application No. 62/552,557, filed on Aug. 31, 2017.

(51) Int. Cl.
| | |
|---|---|
| *G01N 33/533* | (2006.01) |
| *G01N 33/569* | (2006.01) |
| *G01N 15/14* | (2006.01) |
| *G01N 33/49* | (2006.01) |
| *G01N 33/53* | (2006.01) |
| *G01N 33/58* | (2006.01) |
| *G01N 15/10* | (2006.01) |

(52) U.S. Cl.
CPC .......... *G01N 33/533* (2013.01); *G01N 15/14* (2013.01); *G01N 33/49* (2013.01); *G01N 33/5306* (2013.01); *G01N 33/56966* (2013.01); *G01N 33/582* (2013.01); *G01N 15/1459* (2013.01); *G01N 2015/1006* (2013.01)

(58) Field of Classification Search
CPC .............. G01N 15/14; G01N 15/1459; G01N 2015/1006; G01N 33/49; G01N 33/5306; G01N 33/533; G01N 33/56966; G01N 33/582
See application file for complete search history.

(56) References Cited

U.S. PATENT DOCUMENTS

| | | |
|---|---|---|
| 4,876,190 A | 10/1989 | Recktenwald |
| 2006/0160998 A1 | 7/2006 | Suk |
| 2010/0151493 A1 | 6/2010 | Wolfers et al. |
| 2012/0165213 A1 | 6/2012 | Van Dongen et al. |
| 2012/0231473 A1 | 9/2012 | Han |

FOREIGN PATENT DOCUMENTS

WO     9944067 A1     9/1999

OTHER PUBLICATIONS

A printout "Phycobiliproteins" retrieved from https://www.agilent.com/store/en_US/LCat-SubCat2ECS_655142/Phycobiliproteins on Jan. 30, 2020.*
Burroughs, "PhycoLink® Conjugation and Purification Kits," presented at ISAC XXIII International Congress, May 23, 2006, pp. 1-45.*
McKinnon, "Flow Cytometry: An Overview," Curr. Protoc. Immunol., Feb. 21, 2018; 120: 5.1.1-5.1.11.*
International Search Report and Written Opinion dated Dec. 14, 2018, Application No. PCT/US2018/047897, 14 pages.
Schulte, T. et al., "Structure and function of native and refolded peridinin-chlorophyll-proteins from dinoflagellates," Eur. J. Cell Biol., 2010, vol. 89(12), pp. 990-997.
Miller, D.J. et al., "Reconstitution of the Pendinin—chlorophyll a Protein (PCP): Evidence for Functional Flexibility in chlorophyll Binding," Photosynthesis Research, 2005, vol. 86, pp. 229-240.
Schulte, Tim, et al., "Identification of a single peridinin sensing Chl-a excitation in reconstituted PCP by crystallography and spectroscopy," PNAS, Dec. 8, 2009, 20764-20769, vol. 106, No. 49.
Jiang, Tao, et al., "Structure and Function of Chromophores in R-Phycoerythrin at 1.9 Å Resolution," Proteins: Structure, Function, and Genetics, 34:224-231 (1999), Wiley-Liss, Inc.
Glazer, et al., "Biliproteins of Cyanobacteria and Rhodophyta: Homologous Family of Photosynthetic Accessory Pigments", Proc. Nat. Acad. Sci., vol. 73, No. 2, Feb. 1976, 428-431.
Hofmann, et al., "Structural Basis of Light Harvesting by Carotenoids: Peridinin-Chlorophyll-Protein from Amphidinium Carterae", Science, vol. 272, Jun. 21, 1996, 1788-1791.
Chan, et al. "Stabilization of Pre-Optimized Multicolor Antibody Cocktails for Flow Cytometry Applications", Cytometry, Part B (Clinical Cytometry), vol. 92, No. 6, May 11, 2016, 508-524.
Dale, "Rapid Production of Quasi-Stable Antibody-Phycoerythrin Conjugates for Use in Flow Cytometry", Cytometry, vol. 33, No. 4, Dec. 1, 1998, 482-486.
Extended European Search Report dated Apr. 22, 2021, Application No. 18849913.1, 8 pages.

* cited by examiner

*Primary Examiner* — Galina M. Yakovleva

(57) ABSTRACT

The present disclosure is directed to formulations and methods that can be used for flow cytometry analysis. The present formulations and methods involve the use of PerCP to stabilize fluorochromes used in flow cytometry, allowing for use and storage of formulations at elevated temperatures and/or over long periods of time.

21 Claims, 12 Drawing Sheets

COMPOSITION FOR STABILIZATION OF ANTIBODY FORMULATIONS CONTAINING PERCP

PRIORITY CLAIM

This application claims priority to and the benefit of U.S. Provisional Patent Application No. 62/552,557, filed Aug. 31, 2017, the entire contents of which are incorporated herein by reference.

FIELD OF THE INVENTION

The present disclosure is directed to formulations, methods, and kits which comprise stable binding agents.

BACKGROUND

Flow cytometry is a powerful method used to characterize properties of individual cells, as well as to identify types of cells in heterogeneous mixtures. Cells are generally stained by preparing a suspension from a cell culture or tissue sample, and incubating the cells in tubes or microtiter plates with unlabeled or fluorochrome-labeled antibodies. The suspension is introduced into a flow cytometer, and a flow of the cells are irradiated with a laser beam. The fluorescence emission and light scattering caused by interaction between a cell and the laser beam are detected, and one or more characteristics of the cell are quantified based on the measured fluorescence emission and/or scattering.

Flow cytometry also allows for identification, quantification, separation, and/or isolation of individual cells based on measured optical properties. This method is known as immunophenotyping, and can be used to analyze multiple cell populations in a heterogeneous mixture. Immunophenotyping can be accomplished by introducing an antibody capable of binding to a cellular marker to cells comprising the cellular marker and detecting any resulting fluorescence or scattering using flow cytometry. If a cell marker is expressed in more than one cell type, multiple antibodies can be added to the heterogeneous mixture to effectively differentiate the populations. In such cases, each antibody is conjugated to a different fluorochrome, allowing for detection of multiple markers simultaneously. For example, an antibody conjugated to a first fluorochrome and an antibody conjugated to second fluorochrome can be added to a heterogeneous mixture and analyzed by flow cytometry to detect, measure, and sort two different cell populations. The use of multiple fluorochromes in a flow cytometry process is known as multicolor flow cytometry. In some instances, multicolor flow cytometry utilizes the same fluorochrome on one or more antibodies, e.g., when the similarly labeled antibodies recognize epitopes on different cell types.

Various types of fluorochromes can be used in a flow cytometry method. For example, single fluorochromes, which are generally organic compounds or proteins, can be conjugated to a binding agent. Typical single fluorochromes used in flow cytometry include fluorescein isothiocyanate (FITC), R-phycoerythrin (R-PE), allophycocyanin (APC), and peridinin chlorophyll protein complex (PerCP). Tandem fluorochromes where two fluorochromes are attached to each other can also be conjugated to an antibody. Tandem fluorochromes comprise a fluorochrome donor and a fluorochrome acceptor. When the donor is excited by light, it emits energy that is transferred to the acceptor. The second fluorochrome reaches an excited state, and produces a fluorescence emission that can be detected and measured. Typical donors include PerCP, R-PE, and APC, while typical acceptors include ALEXA FLUOR® fluorochromes and cyanine fluorochromes. Tandem fluorochromes generally provide greater brightness than single fluorochromes. However, tandem fluorochromes are often light sensitive and require reduction or minimization of light exposure during cell labeling and flow cytometry analysis.

Peridinin-chlorophyll protein complexes (PerCP) are carotenoid-protein complexes that were first disclosed over 100 years ago. The peridinin molecules of PerCP absorb light in the blue-green wavelengths (470 to 550 nm) and transfer energy to the chlorophyll molecules with high efficiency. PerCP has an extremely high extinction coefficient, a high quantum efficiency and a large Stokes shift. PerCP protein is commonly used in fluorescent immunolabeling applications such as fluorescent-activated cell sorting (FACS). The properties of PerCP and related conjugates render these complexes useful for multicolor analysis with FITC, PE, and other fluorochromes.

PerCP may be used alone or in a tandem fluorochrome. For example, PerCP may be attached to a cyanine (e.g., Cy5.5) to form a PerCP-Cy tandem fluorochrome (e.g., PerCP-Cy5.5). Cy5.5® is a registered trademark of Amersham Bioscience Corporation, now GE Healthcare. Cyanine tandems of PerCP (e.g., PerCP-Cy5.5) can be excited with a standard 488 nm laser. For example, PerCP-Cy5.5 has a maximum fluorescence emission at a wavelength of 694 nm and unconjugated PerCP at a wave length of 677 nm. For immunophenotyping analysis, a PerCP-Cy moiety may be linked to an antibody that specifically binds to a desired target. However, a disadvantage of using PerCP fluorochromes is their inherent instability. PerCP formulations are typically stored at temperatures below 8° C. to maintain stability. Great care must be taken when using PerCP formulations or when transporting PerCP formulations, as the formulation will decompose at higher temperatures. If the transport of PerCP formulation is delayed or the PerCP formulation is accidentally left unrefrigerated, resulting in temperature increase, the PerCP fluorochrome rapidly decays. Since PerCP fluorochromes are provided to customers as liquid formulations having a known and labeled concentration, any degradation of the fluorochrome can lead to experimental error. Such an occurrence necessitates a new batch, which could cause a delay in medical diagnosis or prognosis.

Accordingly, there is a need for new formulations and methods for increasing the stability of PerCP fluorochromes. Such formulations and methods ideally will enhance stability of the PerCP fluorochrome without interfering with the fluorescence properties of the fluorochrome in flow cytometric analysis.

SUMMARY OF THE INVENTION

In an embodiment, the present disclosure provides a stable formulation. The stable formulation comprises (a) at least one labeled binding agent comprising a binding moiety and a conjugated fluorochrome, and (b) unconjugated peridinin chlorophyll protein complex (PerCP) or a fragment or variant thereof, wherein the formulation has a total PerCP concentration of at least about 0.1 µg/mL. In some embodiments, the conjugated fluorochrome is a PerCP tandem fluorochrome. In some embodiments, the conjugated fluorochrome is peridinin chlorophyll protein-cyanine 5.5 (PerCP-Cy5.5). In some embodiments, the conjugated fluorochrome is a PerCP. In some embodiments, the unconjugated PerCP or a fragment or variant thereof is at a concentration of at least about 50 µg/mL. In some embodiments, the antibody is an anti-CD19 antibody, an anti-CD34 antibody, or an anti-MPO antibody. In some embodiments, the ratio of the unconjugated PerCP or a fragment or variant thereof to the labeled binding agent is at least about 2:1. In some embodiments, the unconjugated PerCP is a full-length PerCP. In some embodiments, the unconjugated PerCP or a fragment or variant thereof is a peridinin chlorophyll protein complex that is not attached or bound to another chemical moiety. In some embodiments, the formulation has greater stability than a formulation having no unconjugated PerCP or a fragment or variant thereof. In some embodiments, the fluorescence intensity of the formulation changes by about 25% or less at a temperature of about 20° C. for about 1 day to about 180 days. In some embodiments, the labeled binding agent in the presence of unconjugated PerCP or a fragment or variant thereof has a change in fluorescence intensity of about 25% or less when the temperature of the formulation is increased by at least about 10° C.

In another embodiment, the present disclosure provides a method of analyzing a sample using flow cytometry. The method comprises contacting a sample comprising cells with a formulation comprising (a) at least one labeled binding agent comprising a binding moiety and a conjugated fluorochrome, and (b) unconjugated peridinin chlorophyll protein complex (PerCP) or a fragment or variant thereof to form an analytical sample, and analyzing the analytical sample using flow cytometry. The formulation has a total PerCP concentration of at least about 0.1 µg/mL. In some embodiments, the conjugated fluorochrome is a PerCP tandem fluorochrome. In some embodiments, the conjugated fluorochrome is peridinin chlorophyll protein-cyanine 5.5 (PerCP-Cy5.5). In some embodiments, the conjugated fluorochrome is a PerCP. In some embodiments, the formulation has a total concentration of PerCP or a fragment or variant thereof of at least about 75 µg/mL. In some embodiments, the method further comprises sorting cells in the cell composition based on fluorescence emission of the fluorochrome. In some embodiments, the antibody is an anti-CD19 antibody, an anti-CD34 antibody, or an anti-MPO antibody. In some embodiments, the cells are human blood cells. In some embodiments, the contacting is performed at a temperature of at least about 20° C.

In another embodiment, the present disclosure provides a kit for analyzing cells in a flow cytometer. The kit comprises (a) at least one labeled binding agent comprising a binding moiety and a conjugated fluorochrome, and (b) unconjugated peridinin chlorophyll protein complex (PerCP) or a fragment or variant thereof. In some embodiments, the conjugated fluorochrome is peridinin chlorophyll protein-cyanine 5.5 (PerCP-Cy5.5) and the kit is stored at a temperature of at least about 20° C.

In another embodiment, the present disclosure provides a method of stabilizing at least one labeled binding agent. The method comprises adding unconjugated peridinin chlorophyll protein complex (PerCP) or a fragment or variant thereof to at least one labeled binding agent comprising a binding moiety and a conjugated fluorochrome to form a stable formulation. The stable formulation has a total PerCP concentration of at least about 0.1 µg/mL.

In another embodiment, the present disclosure provides a stable bead formulation that may be used with flow cytometry. The stable bead formulation comprises (a) at least one PerCP-labeled or PerCP-Cy5.5-labeled bead, (b) unconjugated PerCP or a fragment or variant thereof, and (c) a liquid, wherein the formulation has a total PerCP concentration of at least about 0.1 µg/mL.

These and other features and advantages of the present formulations and methods will be apparent from the following detailed description, in conjunction with the appended claims.

DEFINED TERMINOLOGY

It is to be understood that the terminology used herein is for purposes of describing particular embodiments only, and is not intended to be limiting. The defined terms are in addition to the technical and scientific meanings of the defined terms as commonly understood and accepted in the technical field of the present teachings.

The term "fluorochrome" refers to a moiety capable of being detected colorimetrically or fluorometrically. The term "conjugated fluorochrome" refers to a fluorochrome that has been conjugated (e.g., linked or covalently bound to) a binding moiety.

The term "stable" refers to a compound or composition in which the fluorescence properties of the compound or composition do not vary greatly. In some embodiments, the fluorescence intensity of a stable compound or composition varies by about 25% or less, about 10% or less, about 5% or less, about 1% or less, or about 0.1% or less when the temperature is varied (e.g., temperature increase of about 40° C., about 30° C., about 20° C., about 10° C., or about 5° C.).

The term "binding moiety" refers to a moiety capable of binding to a target. Nonlimiting examples include an antibody or a nucleic acid probe.

The term "labeled" refers to a moiety (e.g., an antibody) that has an attached fluorochrome.

The term "total concentration of PerCP" or "total concentration of peridinin chlorophyll protein complex" or "total PerCP concentration" refers to the total amount (moles or mass) of PerCP or a fragment or variant thereof in a formulation divided by the total volume of the formulation. The total amount of PerCP is the sum of the amount of unconjugated PerCP and/or a fragment or variant thereof and the amount of PerCP in labeled binding agent.

The terms "unconjugated peridinin chlorophyll protein" or "free PerCP" are used interchangeably herein and refer to peridinin chlorophyll protein complex or a fragment or variant thereof that is not bound to an antibody or nucleic acid probe.

As used in the specification and appended claims, and in addition to their ordinary meanings, the terms "substantial" or "substantially" mean to within acceptable limits or degree to one having ordinary skill in the art. For example, "substantially cancelled" means that one skilled in the art considers the cancellation to be acceptable.

As used in the specification and the appended claims and in addition to its ordinary meaning, the terms "approximately" and "about" mean to within an acceptable limit or amount to one having ordinary skill in the art. The term "about" generally refers to plus or minus 15% of the indicated number. For example, "about 10" may indicate a range of 8.5 to 11.5. For example, "approximately the same" means that one of ordinary skill in the art considers the items being compared to be the same.

In the present disclosure, numeric ranges are inclusive of the numbers defining the range. In the present disclosure, wherever an embodiment is described as "comprising" a particular feature, the present disclosure also contemplates other embodiments which "consist essentially of" that feature or which "consist of" that feature. It should be recognized that chemical structures and formula may be elongated or enlarged for illustrative purposes.

Unless defined otherwise, all technical and scientific terms used herein have the same meaning as commonly understood by those working in the fields to which this disclosure pertain.

BRIEF DESCRIPTION OF THE DRAWINGS

The present teachings are best understood from the following detailed description when read with the accompanying drawing figures. The features are not necessarily drawn to scale.

FIGS. 1A-1E show flow cytometry side scatter plots of blood treated with anti-CD19/PerCP-Cy5.5. FIGS. 1F-1J show histograms of lymphocytes that were gated on a anti-CD45/pacific blue scatter plot.

FIGS. 3A-3D show histograms of lymphocytes from anti-CD19/PerCP-Cy5.5 stained blood, while FIGS. 3E-3H show histograms of lymphocytes from anti-CD3/PerCP (an anti-human CD3 antibody conjugated with PerCP) stained blood.

FIGS. 4A-4D show results of using 50 µg/mL anti-CD19/PerCP-Cy5.5 and 130 µg/mL unconjugated PerCP, and FIG. 4E-4H show results using the same reagent in a 4 times dilution; 12.5 µg/mL anti-CD19/PerCP-Cy5.5 supplemented with 32.5 µg/mL unconjugated PerCP.

DETAILED DESCRIPTION

Figure 1:
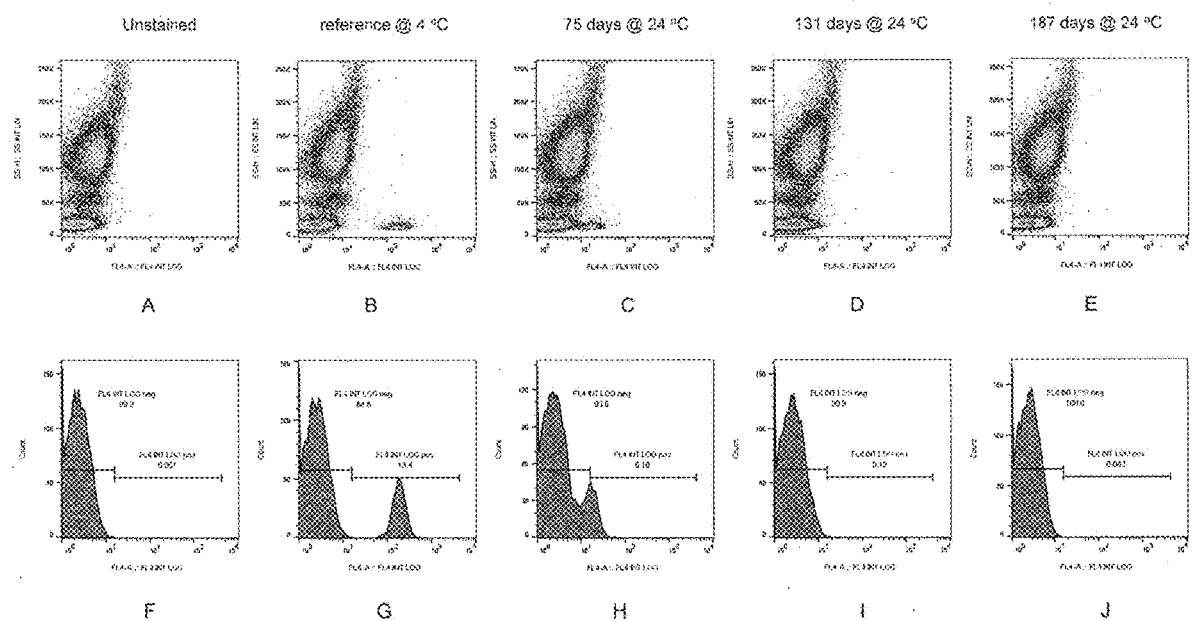
FIGS. 1A-1J are graphs showing flow cytometry data for accelerated stability testing of the binding agent anti-CD19/PerCP-Cy5.5, which comprises an anti-human CD19 antibody conjugated with the fluorochrome PerCP-Cy5.5.

Before the various embodiments are described, it is to be understood that the teachings of this disclosure are not limited to the particular embodiments described, and as such can, of course, vary. It is also to be understood that the terminology used herein is for the purpose of describing particular embodiments only, and is not intended to be limiting, since the scope of the present teachings will be limited only by the appended claims.

As disclosed herein, a number of ranges of values are provided. It is understood that each intervening value, to the tenth of the unit of the lower limit, unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither, or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present teachings, some exemplary methods and materials are now described.

All patents and publications referred to herein are expressly incorporated by reference in their entireties. The citation of any publication is for its disclosure prior to the filing date and should not be construed as an admission that the present claims are not entitled to antedate such publication. Further, the dates of publication provided can be different from the actual publication dates which can be independently confirmed.

As used in the specification and appended claims, the terms "a", "an," and "the" include both singular and plural referents, unless the context clearly dictates otherwise. Thus, for example, "a moiety" includes one moiety and plural moieties.

As will be apparent to those of skill in the art upon reading this disclosure, each of the individual embodiments described and illustrated herein has discrete components and features which can be readily separated from or combined with the features of any of the other several embodiments without departing from the scope or spirit of the present teachings. Any recited method can be carried out in the order of events recited or in any other order which is logically possible.

Formulations and methods are provided which increase the stability of labeled binding agents. Formulations comprising unconjugated peridinin chlorophyll protein complexes (PerCP) or fragments or variants thereof and a labeled binding agent comprising a binding moiety and a conjugated fluorochrome (e.g., an antibody conjugated to a fluorochrome) have increased stability when compared to formulations having no unconjugated PerCP. It has been unexpectedly discovered that having PerCP or a fragment or variant thereof at or above a certain concentration in the formulation increases the stability of the labeled binding agent. The presence of unconjugated PerCP or a fragment or variant thereof at sufficient concentration results in a labeled binding agent having increased temperature stability. PerCP formulations are commonly stored at a temperature of 2-8° C. An advantage of some embodiments of the present formulations is that they can be stored at temperatures above 8° C. (e.g., at room temperature) without substantial degradation of the labeled binding agent. As a result, some embodiments of the formulations of the present disclosure can be prepared well in advance of use. Another advantage of some embodiments of the present formulations is that the labeled binding agent can be of low concentration without compromising stability. The present formulations and methods can employ a range of fluorochromes including single or tandem fluorochromes (e.g., a single or tandem PerCP). The labeled binding agent comprising a binding moiety and a conjugated fluorochrome can be used to detect a variety of cellular targets.

In an embodiment, the present disclosure provides a stable formulation. The stable formulation comprises (a) at least one labeled binding agent comprising a binding moiety and a conjugated fluorochrome, and (b) unconjugated peridinin chlorophyll protein complex (PerCP) or a fragment or variant thereof, wherein the formulation has a total PerCP concentration of at least about 0.1 µg/mL.

In another embodiment, the present disclosure provides a method of stabilizing at least one labeled binding agent. The method comprises adding unconjugated PerCP or a fragment or variant thereof to at least one labeled binding agent comprising a binding moiety and a conjugated fluorochrome to form a stable formulation. The stable formulation has a total PerCP concentration of at least about 0.1 µg/mL.

In some embodiments, the fluorochrome is a single fluorochrome. In some embodiments, the fluorochrome is a tandem fluorochrome.

In some embodiments, the fluorochrome comprises, consists essentially of or consists of a PerCP or a fragment or variant thereof. In some embodiments, the fluorochrome is a tandem fluorochrome comprising PerCP. In some embodiments, the fluorochrome is a tandem fluorochrome comprising a PerCP-cyanine. In some embodiments, the cyanine is selected from isothiocyanines, benzindodicarbocyanines, indocarbocyanines, benzindocarbocyanines, indodicarbocyanines, indotricarbocyanines, benzindo-dicarbocyanines, thiazole orange, oxazole yellow, CYA (3-(epsilon-carboxypentyl)-3' ethyl-5,5'-dimethyloxacarbocyanine), and merocyanines. In some embodiments, the cyanine is selected from Cy5, Cy5.5, Cy3, Cy 3.5, Cy 7, and Cy7.5. In some embodiments, the fluorochrome is PerCP-Cy5.5.

In some embodiments, the fluorochrome has a maximum fluorescence emission at a wavelength different than the maximum fluorescence emission of PerCP or a fragment or variant thereof. For example, a fluorochrome comprising a PerCP or a fragment or variant thereof in tandem with a cyanine has a maximum fluorescence emission at a wavelength that is different than that of PerCP or a fragment or variant thereof alone.

PerCP comprises a peridinin-chlorophyll protein bound to peridinin, chlorophyll, and lipids. PerCP protein may exist in a homodimeric form having two monomers, a monomeric form generated from the homodimeric form via gene duplication, or a trimeric form generated from three copies of monomeric PerCP. In some embodiments, the formulation comprises unconjugated PerCP or a conjugated fluorochrome comprising a PerCP protein in a homodimeric form. In some embodiments, the formulation comprises unconjugated PerCP or a conjugated fluorochrome comprising a PerCP protein in a monomeric form. In some embodiments, the formulation comprises unconjugated PerCP or a conjugated fluorochrome comprising a PerCP protein in a trimeric form. In some embodiments, the formulation comprises unconjugated PerCP or a conjugated fluorochrome comprising a PerCP protein in homodimeric form, monomeric form, trimeric form, or a combination thereof. In some embodiments, the homodimeric, monomeric, and trimeric forms are expressed by different genes.

PerCP proteins can exist as various isoforms or variants. For example, PerCP proteins may have different lengths, sequences, or fold structures. In some embodiments, the formulation comprises unconjugated PerCP or a conjugated fluorochrome comprising a PerCP protein comprising one or more variants of PerCP protein.

In some embodiments, the PerCP comprises a PerCP fragment. In some embodiments, the formulation comprises unconjugated PerCP or a conjugated fluorochrome comprising at least one fragment of a PerCP protein. In some embodiments, the formulation comprises unconjugated PerCP or a conjugated fluorochrome comprising a fragment having a substantial sequence identity with PerCP protein, but that is not identical to PerCP protein. In some embodiments, the fragment comprises at least about 60%, at least about 75%, at least about 85%, at least about 90%, at least about 95%, at least about 96%, at least about 97%, at least about 98%, at least about 99%, at least about 99.5%, or about least about 99.9% of the sequence of full-length PerCP protein. However, the PerCP fragment may have any length consistent with the uses described herein.

In some embodiments, the PerCP comprises a PerCP variant having at least one amino acid deletion, insertion, or substitution relative to the wildtype PerCP protein. In some embodiments, the PerCP variant has at least about 50%, at least about 60%, at least about 70%, at least about 80%, at least about 90%, at least about 95%, or more than 95% amino acid identity to the amino acid sequence of the wild type PerCP protein. However, the PerCP variant may have any degree of amino acid identity with the wild type PerCP protein consistent with the uses described herein. In some embodiments, the degree of amino acid identity may be determined using BLASTP with the default parameters.

In some embodiments, the unconjugated PerCP or a conjugated fluorochrome comprises the full-length PerCP protein.

The molar ratio of peridinin to chlorophyll may vary in the PerCP or a fragment or variant thereof. In some embodiments, the molar ratio of peridinin to chlorophyll is from about 1:1 to about 6:1. In some embodiments, the molar ratio of peridinin to chlorophyll is from about 3:1 to about 6:1. In some embodiments, the molar ratio of peridinin to chlorophyll is from about 3:1 to about 4:1. In some embodiments, the molar ratio of peridinin to chlorophyll is about 4:1. In some embodiments, the molar ratio of peridinin to chlorophyll is about 6:1. In some embodiments, the molar ratio of peridinin to chlorophyll is about 3:1.

In some embodiments, the unconjugated PerCP or a fragment or variant thereof is a peridinin chlorophyll protein complex or a fragment or variant thereof that is not attached or bound to another chemical moiety. In some embodiments, the unconjugated PerCP or a fragment or variant thereof is a peridinin chlorophyll protein complex or a fragment or variant thereof that is not covalently attached to another chemical moiety.

Unconjugated PerCP or a fragment or variant thereof can be used in any suitable amount. In some embodiments, the formulation comprises unconjugated PerCP or a fragment or variant thereof at a concentration of at least about 0.1 µg/mL. Thus, in some embodiments, the formulation comprises unconjugated PerCP or a fragment or variant thereof at a concentration of at least about 0.1 µg/mL, at least about 0.5 µg/mL, at least about 1 µg/mL, at least about 5 µg/mL, at least about 10 µg/mL, at least about 20 µg/mL, at least about 25 µg/mL, at least about 30 µg/mL, at least about 40 µg/mL, at least about 50 µg/mL, at least about 60 µg/mL, at least about 75 µg/mL, at least about 80 µg/mL, at least about 90 µg/mL, at least about 100 µg/mL, at least about 110 µg/mL, at least about 120 µg/mL, at least about 125 µg/mL, at least about 130 µg/mL, at least about 150 µg/mL, at least about 175 µg/mL, or at least about 200 µg/mL. In some embodiments, the formulation comprises unconjugated PerCP or a fragment or variant thereof at a concentration of from about 0.1 µg/mL to about 250 µg/mL. In some embodiments, the formulation comprises unconjugated PerCP or a fragment or variant thereof at a concentration of from about 10 µg/mL to about 500 µg/mL. In some embodiments, the formulation comprises unconjugated PerCP or a fragment or variant thereof at a concentration of from about 25 µg/mL to about 250 µg/mL. In some embodiments, the formulation comprises unconjugated PerCP or a fragment or variant thereof at a concentration of from about 50 µg/mL to about 200 µg/mL.

In some embodiments, the binding moiety is an antibody. The antibody may be an anti-human, anti-mouse, anti-rat, anti-goat, or anti-non-human primate antibody.

In some embodiments, the binding moiety is a monoclonal, polyclonal, synthetic, or recombinant antibody. In some embodiments, the binding moiety is an IgG, IgM, IgA, IgD, or IgE antibody. In some embodiments, the binding moiety is a chimeric or humanized antibody.

In some embodiments, the antibody is selected from an anti-CD19, anti-CD34, anti-CD45, anti-CD1a, anti-CD8, anti-CD2, anti-CD3, anti-CD4, anti-CD5, anti-CD7, anti-CD 9, anti-CD10, anti-CD11a, anti-CD11b, anti-CD11c, anti-CD13, anti-CD14, anti-CD15, anti-CD16, anti-CD16b, anti-CD18, anti-CD19, anti-CD20, anti-CD22, anti-CD23, anti-CD24, anti-CD25, anti-CD27, anti-CD28, anti-CD30, anti-CD33, anti-CD34, anti-CD35, anti-CD36, anti-CD38, anti-CD39, anti-CD41, anti-CD42b, anti-CD43, anti-CD45, anti-CD45RO, anti-CD45RA, anti-CD48, anti-CD 49d, anti-CD50, anti-CD52, anti-CD53, anti-CD54, anti-CD55, anti-CD55, anti-CD56, anti-CD57, anti-CD59, anti-CD61, anti-CD64, anti-CD66, anti-CD68, anti-CD71, anti-CD73, anti-CD79alfa, anti-CD82, anti-CD87, anti-CD90, anti-CD117, anti-CD142, anti-CD236, anti-CD239, anti-CD240, anti-CD241, and anti-CD242 antibody.

In some embodiments, the antibody is an anti-MPO antibody.

In some embodiments, the binding moiety is avidin or steptavidin, and these embodiments are suitable for use with a primary antibody conjugated to biotin (a biotinylated antibody).

The formulations and methods of the present disclosure are particularly useful for stabilizing a formulation comprising a labeled binding agent at low concentration. In some embodiments, the labeled binding agent is present in a solution at a concentration of less than about 200 µg/mL. Thus, in some embodiments, the labeled binding agent is present in a solution at a concentration of less than about 200 µg/mL, less than about 175 µg/mL, less than about 150 µg/mL, less than about 125 µg/mL, less than about 100 µg/mL, less than about 75 µg/mL, less than about 50 µg/mL, or less than about 25 µg/mL. In some embodiments, the labeled binding agent is present in a solution at a concentration of from about 0.01 µg/mL to about 250 µg/mL. In some embodiments, the labeled binding agent is present in a solution at a concentration of from about 1 µg/mL to about 200 µg/mL. In some embodiments, the labeled binding agent is present in a solution at a concentration of from about 0.1 µg/mL to about 100 µg/mL. In some embodiments, the labeled binding agent is present in a solution at a concentration of from about 0.1 µg/mL to about 50 µg/mL. However, the labeled binding agent of the present disclosure can be used at any suitable concentration.

Unconjugated PerCP or a fragment or variant thereof and labeled binding agent can be used at any suitable ratio needed to stabilize the labeled binding agent. In some embodiments, the ratio of unconjugated PerCP or a fragment or variant thereof to labeled binding agent is from about 0.1:1 to about 100:1. In some embodiments, the ratio of unconjugated PerCP or a fragment or variant thereof to labeled binding agent is from about 0.1:1 to about 20:1. Thus, in some embodiments, the ratio of unconjugated PerCP or a fragment or variant thereof to labeled binding agent is from about 0.1:1 to about 20:1, from about 0.5:1 to about 20:1, from about 1:1 to about 20:1, from about 1:1 to about 15:1, from about 1:1 to about 10:1, from about 1:1 to about 8:1, from about 1:1 to about 5:1, or from about 2:1 to about 8:1. In some embodiments, the ratio of unconjugated PerCP or a fragment or variant thereof to a labeled binding agent is at least about 1:1. Thus, in some embodiments, the ratio of unconjugated PerCP or a fragment or variant thereof to labeled binding agent is at least about 1:1, at least about 1.5:1, at least about 2:1, at least about 2.5:1, at least about 3:1, at least about 3.5:1, at least about 4:1, at least about 4.5:1, at least about 5:1, at least about 6:1, at least about 7:1, or at least about 8:1.

In some embodiments, the formulation has a total concentration of PerCP or a fragment or variant thereof of at least about 0.1 µg/mL. Thus, in some embodiments, the formulation has a total concentration of PerCP or a fragment or variant thereof of at least about 0.1 µg/mL, at least about 0.5 µg/mL, at least about 1 µg/mL, at least about 5 µg/mL, at least about 10 µg/mL, at least about 20 µg/mL, at least about 25 µg/mL, at least about 30 µg/mL, at least about 40 µg/mL, at least about 50 µg/mL, at least about 60 µg/mL, at least about 75 µg/mL, at least about 80 µg/mL, at least about 90 µg/mL, at least about 100 µg/mL, at least about 110 µg/mL, at least about 120 µg/mL, at least about 125 µg/mL, at least about 130 µg/mL, at least about 150 µg/mL, at least about 175 µg/mL, or at least about 200 µg/mL. In some embodiments, the formulation has a total concentration of PerCP or a fragment or variant thereof of from about 0.1 µg/mL to about 250 µg/mL. In some embodiments, the formulation a total concentration of PerCP or a fragment or variant thereof of from about 25 µg/mL to about 500 µg/mL. In some embodiments, the formulation has a total concentration of PerCP or a fragment or variant thereof of from about 50 µg/mL to about 500 µg/mL. In some embodiments, the formulation a total concentration of PerCP or a fragment or variant thereof of from about 100 µg/mL to about 400 µg/mL.

In some embodiments, the formulation is a solution. In some embodiments, the formulation is an aqueous solution. In some embodiments, the formulation is a solution comprising an organic solvent.

The formulations of the present disclosure may comprise additional components. In some embodiments, the formulation comprises a buffer, preservative, surfactant, or a combination thereof. In some embodiments, the preservative comprises an isothiazolinone. In some embodiments, the preservative comprises an azide salt. In some embodiments, the preservative comprises an alkaline or alkali earth metal azide. In some embodiments, the preservative comprises sodium azide.

In some embodiments, the formulation comprises a buffer comprising Tris/HCl. In some embodiments, the formulation comprises a buffer comprising sodium chloride. In some embodiments, the formulation comprises a buffer comprising bovine serum albumin. In some embodiments, the formulation comprises about 0.01 M to about 0.2 M Tris/HCl, from about 0.01 M to about 0.4 M sodium chloride, from about 0.1 mM to about 100 mM sodium azide, and from about 0.1% to about 5% bovine serum albumin.

In some embodiments, the formulation comprises a buffer comprising Tris/HCl, NaCl, sodium azide, and bovine serum albumin. In some embodiments, the formulation comprises from about 0.02 M to about 0.08 M Tris/HCl, from about 0.05 M to about 0.2 M sodium chloride, from about 5 mM to about 25 mM sodium azide, from about 0.5% to about 2% bovine serum albumin. In some embodiments, the formulation has a pH of from about 6.5 to about 7.5.

In some embodiments, the formulation comprises at least two labeled binding agents. In some embodiments, the formulation comprises at least three labeled binding agents. In some embodiments, the formulation comprises at least four labeled binding agents. In some embodiments, the formulation comprises at least five labeled binding agents. In such embodiments, the fluorochromes of the various labeled binding agents may be the same or different.

In some embodiments, the formulation comprises at least one labeled binding agent and unconjugated PerCP or a fragment or variant thereof and has greater stability than a formulation having no unconjugated PerCP or a fragment or variant thereof.

In some embodiments, the labeled binding agent in the presence of unconjugated PerCP or a fragment or variant thereof has a change in fluorescence intensity of about 25% or less when the temperature of the formulation is increased by at least about 10° C. for 35-150 days, for example from about 4° C. to about 14° C. for 35-150 days. In some embodiments, the labeled binding agent in the presence of unconjugated PerCP or a fragment or variant thereof has a change in fluorescence intensity of about 25% or less when the temperature of the formulation is increased by at least about 20° C. for 7-180 days for example, from about 4° C. to about 24° C. for 7-180 days or for 20-75 days. In some embodiments, the labeled binding agent in the presence of unconjugated PerCP or a fragment or variant thereof has a change in fluorescence intensity of about 25% or less when the temperature of the formulation is increased by at least about 30° C. for 1-10 days, for example from about 4° C. to about 37° C. or higher for 1-10 days or for 1-3 days.

In some embodiments, the labeled binding agent in the presence of unconjugated PerCP or a fragment or variant thereof has a change in fluorescence intensity of about 20% or less when the temperature of the formulation is increased by at least about 10° C. for 35-150 days, for example from about 4° C. to about 14° C. for 35-150 days. In some embodiments, the labeled binding agent in the presence of unconjugated PerCP or a fragment or variant thereof has a change in fluorescence intensity of about 20% or less when the temperature of the formulation is increased by at least about 20° C. for 7-180 days, for example, from about 4° C. to about 24° C. for 7-180 days or for 20-75 days. In some embodiments, the labeled binding agent in the presence of unconjugated PerCP or a fragment or variant thereof has a change in fluorescence intensity of about 20% or less when the temperature of the formulation is increased by at least about 30° C. for 1-10 days, for example from about 4° C. to about 37° C. or higher for 1-10 days or for 1-3 days.

In some embodiments, the labeled binding agent in the presence of unconjugated PerCP or a fragment or variant thereof has a change in fluorescence intensity of about 10% or less when the temperature of the formulation is increased by at least about 10° C. for 35-150 days, for example from about 4° C. to about 14° C. for 35-150 days. In some embodiments, the labeled binding agent in the presence of unconjugated PerCP or a fragment or variant thereof has a change in fluorescence intensity of about 10% or less when the temperature of the formulation is increased by at least about 20° C. for 7-180 days, for example, from about 4° C. to about 24° C. for 7-180 days or for 20-75 days. In some embodiments, the labeled binding agent in the presence of unconjugated PerCP or a fragment or variant thereof has a change in fluorescence intensity of about 10% or less when the temperature of the formulation is increased by at least about 30° C. for 1-10 days, for example from about 4° C. to about 37° C. or higher for 1-10 days or for 1-3 days.

In some embodiments, the labeled binding agent in the presence of unconjugated PerCP or a fragment or variant thereof has a change in fluorescence intensity of about 5% or less when the temperature of the formulation is increased by at least about 10° C. for 35-150 days, for example from about 4° C. to about 14° C. for 35-150 days. In some embodiments, the labeled binding agent in the presence of unconjugated PerCP or a fragment or variant thereof has a change in fluorescence intensity of about 5% or less when the temperature of the formulation is increased by at least about 20° C. for 7-180 days, for example, from about 4° C. to about 24° C. for 7-180 days or for 20-75 days. In some embodiments, the labeled binding agent in the presence of unconjugated PerCP or a fragment or variant thereof has a change in fluorescence intensity of about 5% or less when the temperature of the formulation is increased by at least about 30° C. for 1-10 days, for example from about 4° C. to about 37° C. or higher for 1-10 days or for 1-3 days.

In some embodiments, the labeled binding agent in the presence of unconjugated PerCP or a fragment or variant thereof has a change in fluorescence intensity of about 1% or less when the temperature of the formulation is increased by at least about 10° C. for 35-150 days, for example from about 4° C. to about 14° C. for 35-150 days. In some embodiments, the labeled binding agent in the presence of unconjugated PerCP or a fragment or variant thereof has a change in fluorescence intensity of about 1% or less when the temperature of the formulation is increased by at least about 20° C. for 7-180 days for example, from about 4° C. to about 24° C. for 7-180 days or for 20-75 days. In some embodiments, the labeled binding agent in the presence of unconjugated PerCP or a fragment or variant thereof has a change in fluorescence intensity of about 1% or less when the temperature of the formulation is increased by at least about 30° C. for 1-10 days, for example from about 4° C. to about 37° C. or higher for 1-10 days or for 1-3 days.

In some embodiments, the formulation is stable at a temperature of about 20° C. for at least about 180 days, in that the fluorescence intensity changes by about 25% or less. In some embodiments, the formulation is stable at a temperature of about 20° C. for at least about 180 days, in that the fluorescence intensity changes by about 20% or less. In some embodiments, the formulation is stable at a temperature of about 20° C. for at least about 180 days, in that the fluorescence intensity changes by about 10% or less. In some embodiments, the formulation is stable at a temperature of about 20° C. for at least about 180 days, in that the fluorescence intensity changes by about 5% or less. Thus, in some embodiments, the formulation is stable at a temperature of about 20° C. for at least about 180 days, at least about 150 days, at least about 120 days, at least about 100 days, at least about 90 days, at least about 80 days, at least about 75 days, at least about 70 days, at least about 60 days, at least about 50 days, at least about 45 days, at least about 40 days, at least about 30 days, at least about 25 days, at least about 20 days, at least about 15 days, at least about 10 days, at least about 7 days, at least about 5 days, at least about 4 days, at least about 3 days, at least about 2 days, or at least about 1 day, in that the fluorescence intensity changes by about 25% or less, about 20% or less, about 10% or less, or about 5% or less.

In some embodiments, the formulation is stable at a temperature of about 20° C. for from about 1 day to about 180 days in that the fluorescence intensity changes by about 25% or less. In some embodiments, the formulation is stable at a temperature of about 20° C. for from about 1 day to about 180 days in that the fluorescence intensity changes by about 20% or less. In some embodiments, the formulation is stable at a temperature of about 20° C. for from about 1 day to about 180 days in that the fluorescence intensity changes by about 10% or less. In some embodiments, the formulation is stable at a temperature of about 20° C. for from about 1 day to about 180 days in that the fluorescence intensity changes by about 5% or less. Thus, in some embodiments, the formulation is stable at a temperature of about 20° C. for from about 1 day to about 180 days, from about 1 day to about 150 days, from about 1 day to about 120 days, from about 1 day to about 100 days, from about 1 day to about 80 days, from about 1 day to about 60 days, from about 1 day to about 45 days, from about 1 day to about 30 days, from about 1 day to about 14 days, from about 1 day to about 7 days, from about 1 day to about 4 days, from about 7 days to about 180 days, from about 14 days to about 180 days, or from about 30 days to about 180 days, in that the fluorescence intensity changes by about 25% or less, about 20% or less, about 10% or less, or about 5% or less.

In some embodiments, the formulation comprises unconjugated PerCP or a fragment or variant thereof and a labeled binding agent comprising PerCP-cyanine (e.g., PerCP-Cy5.5) conjugated fluorochrome. In some embodiments, the unconjugated PerCP or a fragment or variant thereof and the PerCP or a fragment or variant thereof of the conjugated fluorochrome are isolated from the same species. In some embodiments, the unconjugated PerCP or a fragment or variant thereof and the PerCP or a fragment or variant thereof of the conjugated fluorochrome are isolated from different species. In some embodiments, the unconjugated PerCP or a fragment or variant thereof and the PerCP or a fragment or variant thereof of the conjugated fluorochrome are structurally different. In some embodiments, the unconjugated PerCP or a fragment or variant thereof and the PerCP or a fragment or variant thereof of the conjugated fluorochrome are structurally identical.

In some embodiments, the fluorochrome is conjugated to streptavidin or avidin. In some embodiments, a labeled binding agent comprising a streptavidin-conjugated PerCP or tandem PerCP is used in combination with a biotinylated primary antibody.

In another embodiment, the present disclosure provides a method of analyzing a sample using flow cytometry. The method comprises contacting a sample comprising cells with a formulation comprising (a) at least one labeled binding agent comprising a binding moiety and a conjugated fluorochrome, and (b) unconjugated PerCP or a fragment or variant thereof to form an analytical sample, and analyzing the analytical sample using flow cytometry. In some embodiments, the formulation has a total PerCP concentration of at least about 0.1 µg/mL.

The sample may comprise any cell type or preparation. In some embodiments, the sample is a cell culture. In some embodiments, the sample is a cell suspension. For example, the cells of the cell suspension may be derived from solid tissue.

In some embodiments, the sample comprises blood cells. In some embodiments, the sample comprises human blood cells. In some embodiments, the sample comprises leukocytes, such as lymphocytes. In some embodiments, the sample comprises bone marrow cells. In some embodiments, the sample comprises lymphoid organ-derived white cells (e.g. lymph node or spleen). In some embodiments, the sample comprises engineered cells, such as engineered cells used for therapeutic or diagnostic purposes. In some embodiments, the sample comprises CAR-T cells.

In some embodiments, the method further comprises sorting cells in the cell composition based on fluorescence emission of the fluorochrome. In some embodiments, the method further comprises performing cell sorting using fluorescent-activated cell sorting (FACS).

In some embodiments, the cells under analysis are fixed to arrest metabolic process and render the cytoplasm and nucleus accessible to the binding agent, then stained with at least one labeled binding agent.

In some embodiments, the labeled binding agent is a secondary antibody which recognizes a primary antibody.

The present formulations and methods of the present disclosure address the problem of erosion of signal strength of fluorochromes when stored at elevated temperature. The formulations and methods of the present disclosure allow for handling and storage of formulations at various temperatures. In some embodiments, the formulation is contacted with a sample at a temperature of at least about 10° C. Thus, in some embodiments, the formulation is contacted with a sample at a temperature of at least about 10° C., at least about 15° C., at least about 20° C., at least about 25° C., at least about 30° C., at least about 35° C., at least about 40° C., or at least about 40° C.

In some embodiments, the method is a multicolor flow cytometry method.

Methods for operating the flow cytometer, as well as the methods for analyzing the data so acquired, can be varied, and such variations are known and common in the field.

In another embodiment, the present disclosure provides a stable bead formulation that may be used with flow cytometry. The stable bead formulation comprises (a) at least one PerCP-labeled or PerCP-Cy5.5-labeled bead, (b) unconjugated PerCP or a fragment or variant thereof, and (c) a liquid, wherein the formulation has a total PerCP concentration of at least about 0.1 µg/mL. In some embodiments, the liquid is an aqueous liquid. In some embodiments, the liquid is an organic solvent. In some embodiments, the stable beads are CaliBRITE beads. In some embodiments, the beads are latex beads. In some embodiments, the beads are polymethylmethacrylate beads. In some embodiments, the formulation comprises an azide salt.

In another embodiment, the present disclosure provides a kit for analyzing cells in a flow cytometer. The kit comprises (a) at least one labeled binding agent comprising a binding moiety and a conjugated fluorochrome, and (b) unconjugated PerCP or a fragment or variant thereof.

In some embodiments, the kit comprises components (a) and (b) in separate containers. Thus, in some embodiments, the kit comprises at least one labeled binding agent comprising a binding moiety and a conjugated fluorochrome in a first container and unconjugated PerCP or a fragment or variant thereof in a second container.

In some embodiments, the kit further comprises one or more additional compounds suitable for, for example, flow cytometry. In some embodiments, the kit comprises a buffer, preservative, surfactant, or a combination thereof. In some embodiments, the additional compounds are provided in the same or separate containers.

In some embodiments, the kit comprises instructions for using the components of the kit. In some embodiments, the kit comprises instructions for mixing the separate components, suitable conditions for the components and/or mixture, and/or suitable vessels for mixing the composition.

In some embodiments, the kit comprises a "pre-mixed" container comprising a formulation comprising (a) at least one labeled binding agent comprising a binding moiety and a conjugated fluorochrome, and (b) unconjugated peridinin chlorophyll protein complex or a fragment or variant thereof.

EXAMPLE 1

This Example illustrates the effect of temperature and storage on the stability of a labeled binding agent.

The stability of an anti-CD19 antibody conjugated to PerCP-Cy5.5 (i.e., anti-CD19/PerCP-Cy5.5, DAKO) at elevated temperature was examined using an accelerated stability test. The blood of a healthy donor was stained with anti-CD19/PerCP-Cy5.5 in the presence of anti-coagulant EDTA. A 100 µL aliquot of blood was mixed with anti-CD19/PerCP-Cy5.5 and incubated at 2-8° C. in the dark for 30 minutes. A 2 mL portion of FACS lysing solution (BD Biosciences) was mixed with the blood cell composition, and incubated for 10 min in the dark at ambient temperature. The treated blood cells were spun down at 300×g for 5 minutes at ambient temperature. The supernatant was removed. The cells were washed in 2 mL PBS, spun down, and resuspended in 0.4 mL PBS. The samples were analyzed using a Navios flow cytometer (Beckmann Coulter). The cells were co-stained with anti-CD45/Pacific Blue (DAKO). Lymphocytes were gated on side scatter/Pacific blue plots.

The results were compared to untreated cells and cells treated with anti-CD19/PerCP-Cy5.5 at 4° C. Cells were treated with a 25 µg/mL solution of anti-CD19/PerCP-Cy5.5 that was stored at 24° C. for 75, 131, and 187 days (FIG. 1E).

The experimental plots are shown in FIGS. 1A-1J. FIGS. 1A-1E show flow cytometry side scatter plots of blood treated with anti-CD19/PerCP-Cy5.5 at 4° C. or stored at 24° C. for the indicated number of days. FIGS. 1G-1J show histograms of lymphocytes that were gated on a anti-CD45/pacific blue scatter plot. As shown in FIGS. 1B and 1G, there is good separation of anti-CD19 positive and CD19 negative lymphocytes on the histogram when cells are treated with anti-CD19/PerCP-Cy5.5 stored at 4° C. FIGS. 1C and 1H shows that storage of anti-CD19/PerCP-Cy5.5 at 24° C. for 75 days resulted in inadequate separation of CD19 positive and CD19 negative lymphocyte peaks, as evidenced by the merged peaks. FIGS. 1D, 1E, 1I, and 1J show disappearance of the CD19 positive lymphocyte peak in the histograms. The results show that anti-CD19/PerCP-Cy5.5 is not stable at an elevated temperature over an extended period of time.

EXAMPLE 2

This Example illustrates the effect of temperature and concentration on the short time stability of a labeled binding agent.

The stability of anti-CD19/PerCP-Cy5.5 at elevated temperature was examined using a short time stability test. Prior to the experiment, anti-CD19/PerCP-Cy5.5 from DAKO and anti-CD19/PerCP-Cy5.5 from another vendor was stored at 4° C. and 37° C. for 2.5 days at a concentrate of 215 µg/mL and at 25 µg/mL. The blood of a healthy donor was stained and with the stored anti-CD19/PerCP-Cy5.5 and analyzed by flow cytometry using the procedure of Example 1.

Figure 2:
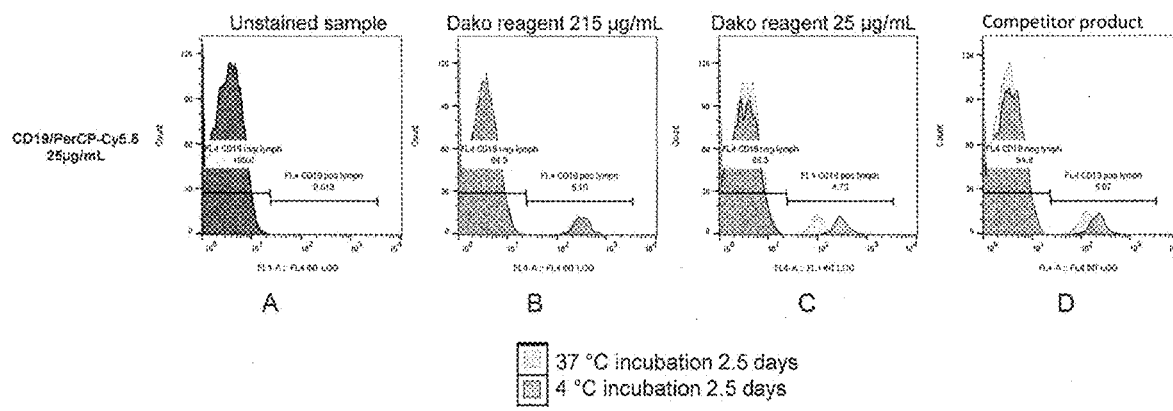
FIGS. 2A-2D are histograms showing flow cytometry data for short time stability testing of anti-CD19/PerCP-Cy5.5 stored at 4° C. and 37° C.

The histograms of lymphocytes are shown in FIGS. 2A-2D, where the signals from the experiment at 4° C. and 37° C. are overlayed. FIGS. 2B and 2C show that the median fluorescence intensity had a greater decrease after incubation with the dilute formulation (i.e., 25 µg/mL anti-CD19/PerCP-Cy5.5) than for the concentrated formulation, which was incubated at 37° C. in a concentrated formulation (215 µg/mL anti-CD19/PerCP-Cy5.5) and diluted to 25 µg/mL just prior to testing by flow cytometry. As shown in FIG. 2D, a decrease in signal was also observed for anti-CD19/PerCP-Cy5.5 obtained from another vendor, which suggests that the observed stability of anti-CD19/PerCP-Cy5.5 is not source-dependent. The results indicate that stability of the PerCP-Cy5.5 conjugate is dependent on concentration of the formulation.

EXAMPLE 3

This Example illustrates the stability of a binding agent-single fluorochrome conjugate and a binding agent-tandem fluorochrome conjugate in the presence of unconjugated PerCP at various concentrations in accordance with an embodiment of the present disclosure.

The stability of anti-CD19/PerCP-Cy5.5 and an anti-CD3 antibody conjugated to PerCP (i.e., anti-CD3/PerCP) in the presence of unconjugated PerCP was examined. Prior to the experiment, anti-CD19/PerCP-Cy5.5 (25 µg/mL) and anti-CD3/PerCP (25 µg/mL) in the presence of unconjugated PerCP was stored for 2 weeks at 4° C. and 37° C. The unconjugated PerCP (PhycoPro™ (PB40) from Prozyme Inc., isolated from Dinophyceae sp.) was used at different concentrations (i.e., 0, 75, 100, and 200 µg/mL). The blood cells of a healthy donor were treated with the stored fluorochromes separately and analyzed by flow cytometry using the procedure of Example 1. A FACSCanto II flow cytometer (BD Biosciences) was used.

The histograms of lymphocytes are shown in FIGS. 3A-3H, where the signals from the experiments using formulations stored at 4° C. and 37° C. are overlayed. FIGS. 3A-3D show histograms of lymphocytes from anti-CD19/PerCP-Cy5.5 stained blood, while FIGS. 3E-3H show histograms of lymphocytes from anti-CD3/PerCP stained blood.

Figure 3:
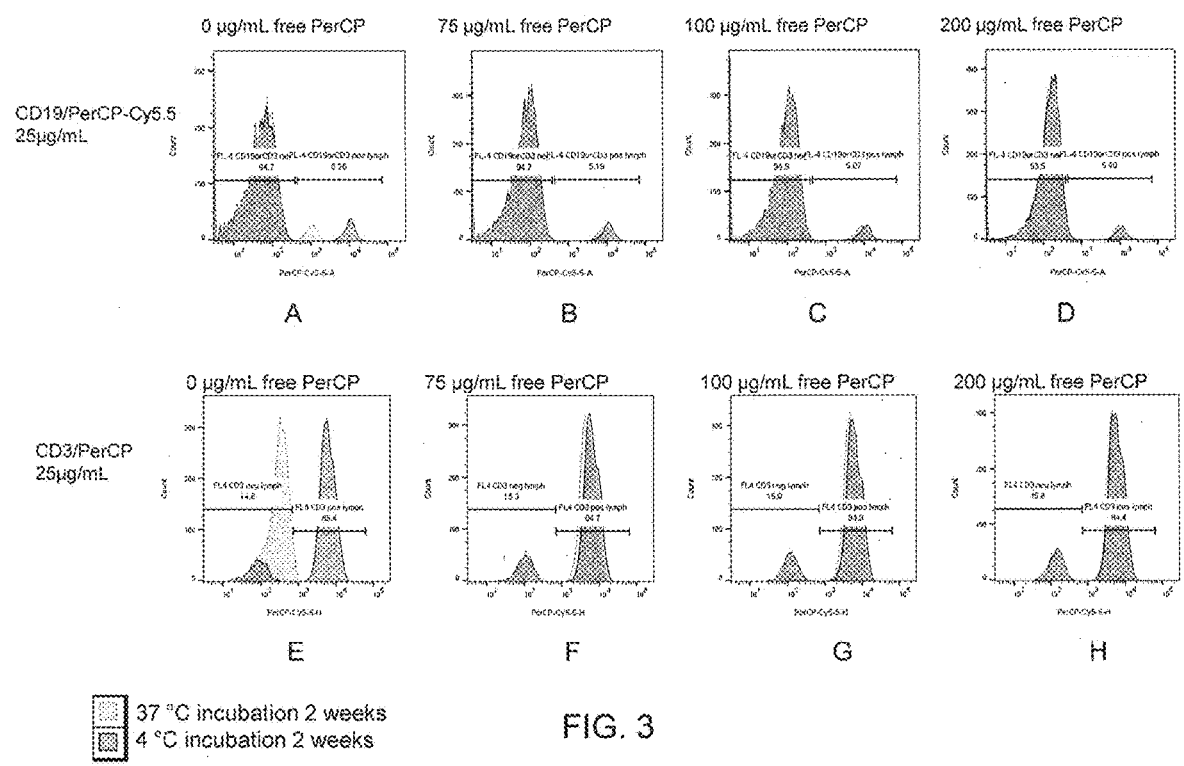
FIGS. 3A-3H show histograms of lymphocytes from stained blood in the absence and presence of unconjugated PerCP.
Figure 4:
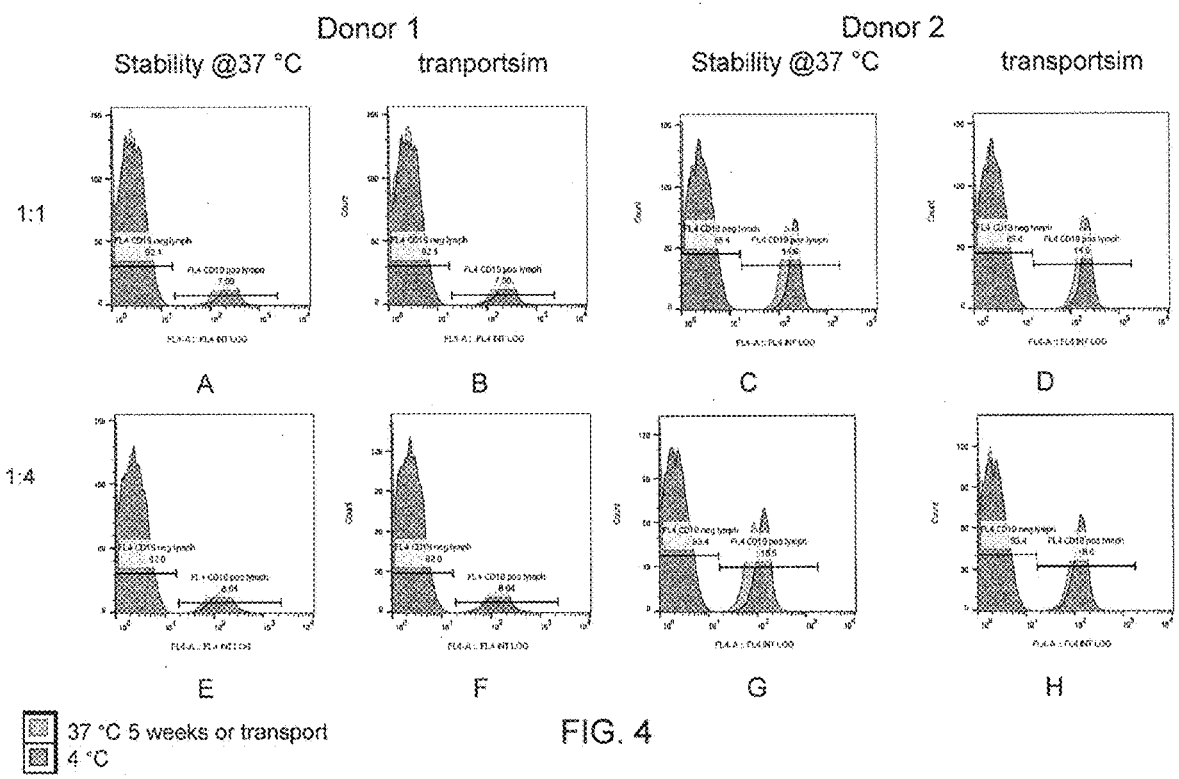
FIGS. 4A-4H are histograms showing flow cytometry data for stability testing of formulations comprising anti-CD19/PerCP-Cy5.5 (50 µg/mL) and unconjugated PerCP (130 µg/mL) used to stain blood at various concentrations.
Figure 5:
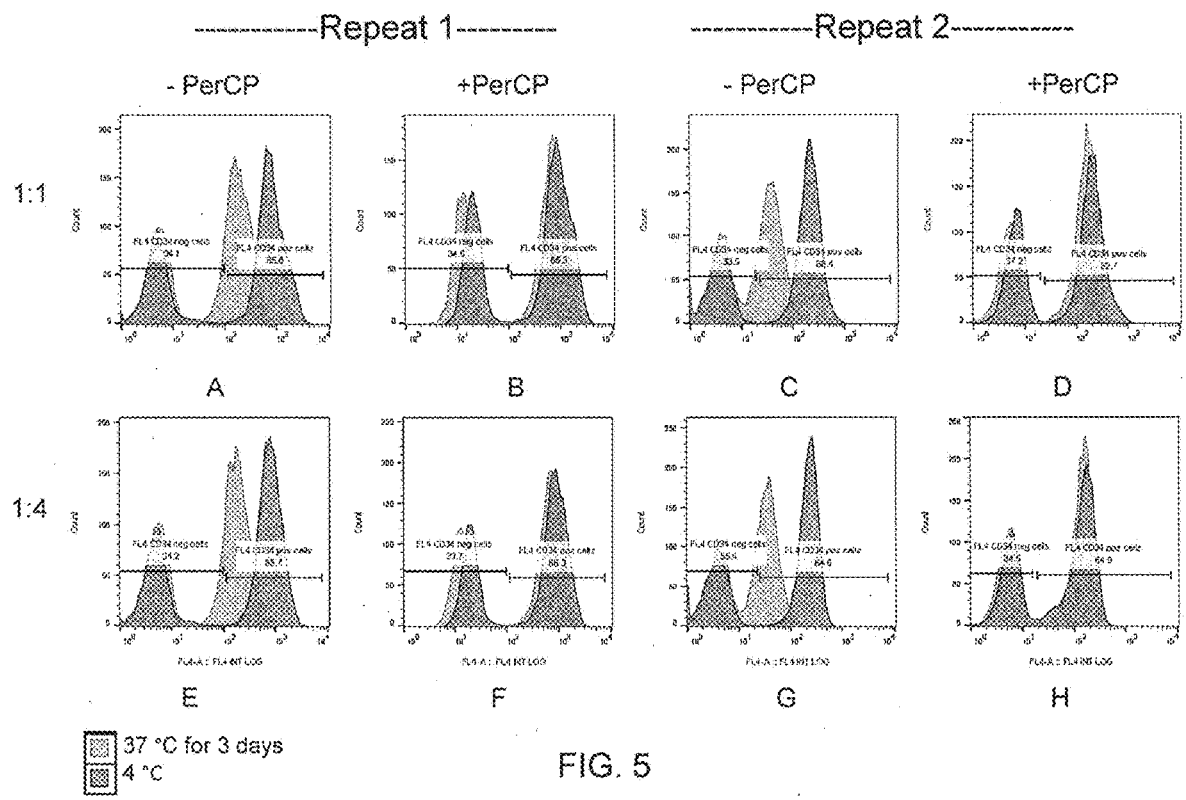
FIGS. 5A-5H are histograms showing flow cytometry data for stability testing of formulations comprising anti-CD34/PerCP-Cy5.5 which comprises an anti-human CD34 antibody conjugated with the fluorochrome PerCP-Cy5.5 in the absence and presence of unconjugated PerCP. The anti-CD34/PerCP-Cy5.5 conjugate was, prior to testing, incubated at 37° C. for 3 days at a reagent concentration of 50 µg/mL with or without 130 µg/mL free PerCP (lighter peaks). A reference was incubated at 4° C. (darker peaks). After incubation, the reagent was tested at a concentration of 130 µg/mL (FIGS. 5A-5D) and 12.5 µg/mL (FIGS. 5E-5H) in the presence of 130 µg/mL and 32.5 µg/mL of unconjugated PerCP respectively (+PerCP) or in the absence of unconjugated PerCP (−PerCP).
Figure 6:
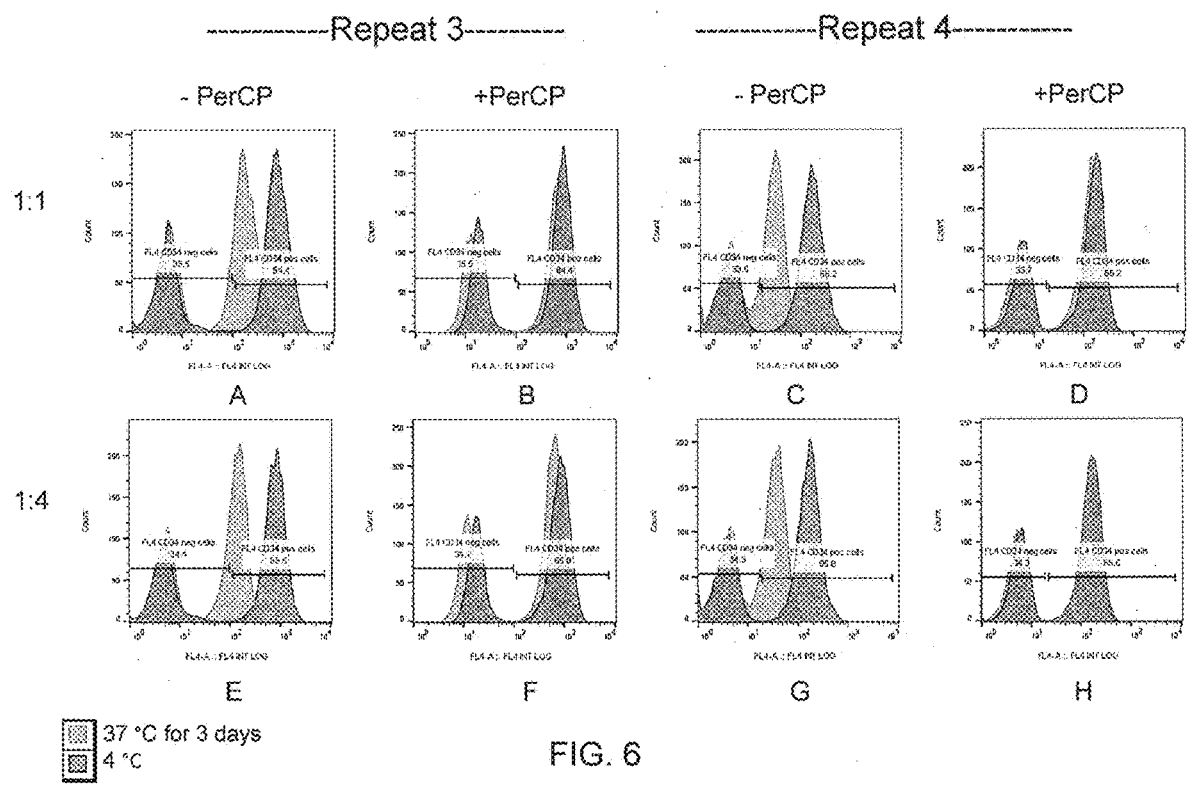
FIGS. 6A-6H are histograms showing flow cytometry data for stability testing of formulations comprising anti-CD34/PerCP-Cy5.5 in the absence and presence of unconjugated PerCP. The experiments of FIGS. 6A-6H are a repeat of the experiments of FIGS. 5A-5H.
Figure 7:
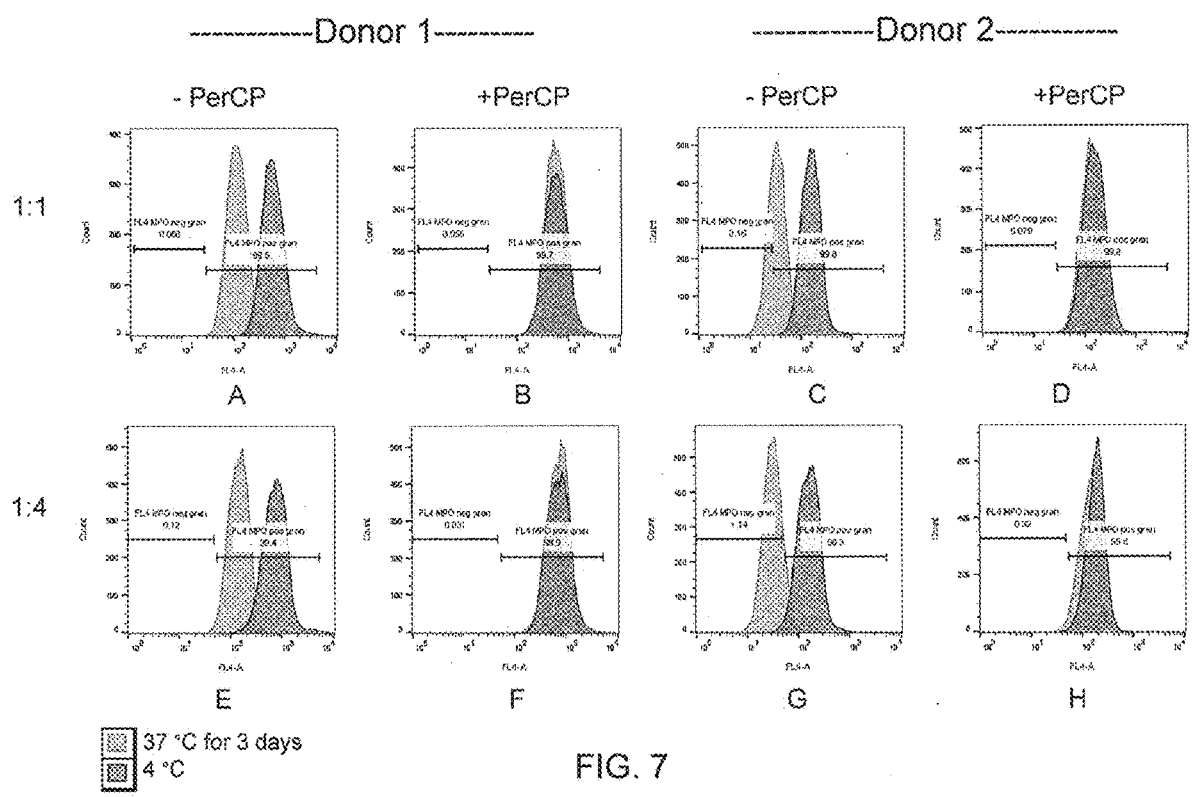
FIGS. 7A-7H are histograms showing flow cytometry data for stability testing of formulations comprising anti-MPO/PerCP-Cy5.5 which comprises an anti-human MPO antibody conjugated with the fluorochrome PerCP-Cy5.5 in the absence and presence of unconjugated PerCP, where the blood samples were procured from two separate donors (i.e., Donor 1 and Donor 2). The anti-MPO/PerCP-Cy5.5 conjugate was tested at a concentration of 50 µg/mL (FIGS. 7A-7D) and 12.5 µg/mL (FIGS. 7E-7H) in the presence of 130 µg/mL and 32.5 µg/mL of unconjugated PerCP (+PerCP), respectively, or in the absence of unconjugated PerCP (−PerCP). Prior to testing, the reagent was incubated at 37° C. for three days at a concentration of 50 µg/mL with or without a supplement of 130 µg/mL unconjugated PerCP (lighter shaded). Similar reagent was stored at 4° C. and used as a reference (darker shaded).
Figure 8:
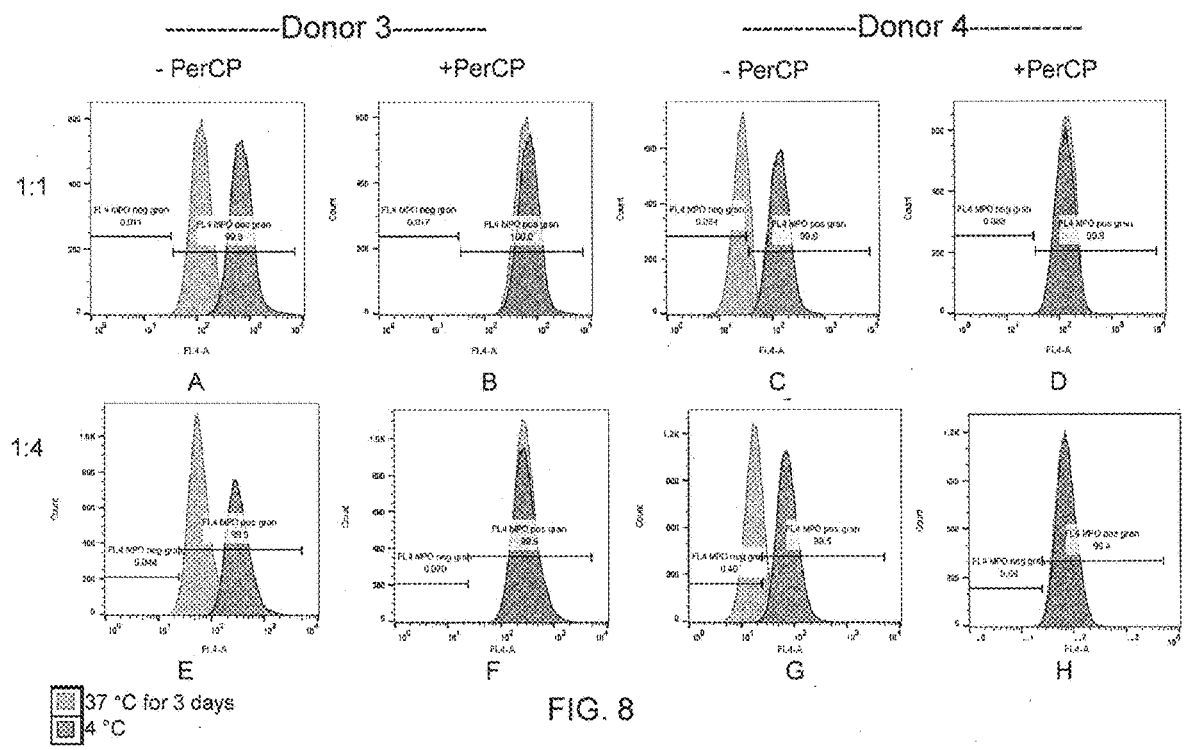
FIGS. 8A-8H are histograms showing flow cytometry data for stability testing of formulations comprising anti-MPO/PerCP-Cy5.5 in the absence and presence of unconjugated PerCP, where the blood samples were procured from two separate donors (i.e., Donor 3 and Donor 4). The anti-MPO/PerCP-Cy5.5 conjugate was tested at a concentration of 50 µg/mL (FIGS. 8A-8D) and 12.5 µg/mL (FIGS. 8E-8H) in the presence of 130 µg/mL and 32.5 µg/mL of unconjugated PerCP (+PerCP), respectively, or in the absence of unconjugated PerCP (−PerCP). The experiments of FIGS. 8A-8H are a repeat of the experiments of FIGS. 7A-7H.

As shown in FIG. 3A, the separation between the CD19 positive and CD19 negative lymphocytes changes when anti-CD19/PerCP-Cy5.5 conjugate stored at 37° C. is used. FIG. 3E shows that use of anti-CD3/PerCP conjugate stored at 37° C. resulted in the disappearance of the signal for CD3 positive lymphocytes. However, when each fluorochrome was stored in the presence of 75 µg/mL of unconjugated PerCP, the histograms for both anti-CD19/PerCP-Cy5.5 and anti-CD3/PerCP were similar at 4° C. and 37° C. as shown in FIGS. 3B and 3F. FIGS. 3C, 3D, 3G, and 3H show that increasing the concentration of PerCP to 100 µg/mL and 200 µg/mL led to further increase in stability for both anti-CD19/PerCP-Cy5.5 and anti-CD3/PerCP. Without wishing to be bound by any particular theory, it is believed that unconjugated PerCP likely stabilizes the PerCP protein of antibody-PerCP conjugates because both anti-CD19/PerCP-Cy5.5 and anti-CD3/PerCP show increased stability in the presence of unconjugated PerCP.

EXAMPLE 4

This Example illustrates the stability of formulations having various concentrations of a labeled binding agent and unconjugated PerCP in accordance with an embodiment of the present disclosure.

The stability of formulations having different concentrations of anti-CD19/PerCP-Cy5.5 and unconjugated PerCP (PhycoPro™ (PB40) from Prozyme Inc., isolated from Dinophyceae sp.) was examined. The tests were conducted using the blood of two different donors (i.e., Donor 1 and Donor 2). The cells were treated with anti-CD19/PerCP-Cy5.5 and analyzed via flow cytometry using the procedure disclosed in Example 1.

The effect of unconjugated PerCP on transport of anti-CD19/PerCP-Cy5.5 was examined using transport simulation. For the transport simulation regime, a sample of anti-CD19/PerCP-Cy5.5 was frozen at −20° C. for 16-24 hours, thawed at 4° C. for 2-8 hours, frozen at −20° C. for 16-24 hours, thawed at 4° C. for 2-8 hours, incubated at 37° C. for 16-24 hours, and incubated at 25° C. for 7 days.

The histograms of lymphocytes are shown in FIGS. 4A-4H. FIGS. 4A-4D show results of using 50 µg/mL anti-CD19/PerCP-Cy5.5 and 130 µg/mL unconjugated PerCP, and FIG. 4E-4H show results using 12.5 µg/mL and anti-CD19/PerCP-Cy5.5 and 32.5 µg/mL unconjugated PerCP. The results demonstrate that the tested formulations have good stability at elevated temperature. The results also suggest that the tested formulations are stable enough to be shipped at ambient temperature.

EXAMPLE 5

This Example illustrates the stability of formulations having various concentrations of a labeled binding agent and unconjugated PerCP in accordance with an embodiment of the present disclosure.

The stability of an anti-CD34 antibody conjugated to PerCP-Cy5.5 (i.e., anti-CD34/PerCP-Cy5.5) at elevated temperature was examined. Prior to the experiment, the anti-CD34/PerCP-Cy5.5 formulations were stored at 4° C.

or 37° C. for 3 days. Anti-CD34/PerCP-Cy5.5 was used to surface stain a cell suspension of 70% KG1a (CD34 positive) and 30% U937 (CD34 negative) cells. The anti-CD34/PerCP-Cy5.5 conjugate was tested at a concentration of 50 µg/mL and 12.5 µg/mL in the presence of 130 µg/mL and 32.5 µg/mL of unconjugated PerCP (+PerCP) (PhycoPro™ (PB40) from Prozyme Inc., isolated from Dinophyceae sp.), respectively, or in the absence of unconjugated PerCP (−PerCP). For each sample, a 100 µL cell suspension containing 1 million cells was mixed with a formulation and stained for 30 min at 2-8° C. in the dark. 2 mL of FACS lysing solution (BD Biosciences) was added. Samples were mixed and incubated for 10 min at ambient temperature in the dark. Cells were spun down 5 min at 300×g at ambient temperature. Supernatant was removed and cells were washed once in 2 mL PBS, spun down, and resuspended in 0.4 mL PBS. Samples were run on the Navios flow cytometer (Beckmann Coulter). Each experiment was repeated three additional times.

The experimental histograms are shown in FIGS. 5A-6H. There was a decrease in median fluorescence intensity for the CD34 positive cells stained with a formulation having no unconjugated PerCP. In contrast, cells stained with anti-CD34/PerCP-Cy5.5 in the presence of unconjugated PerCP provide histograms that are similar when formulations are stored at 4° C. and 37° C. The results demonstrate that unconjugated PerCP increases the stability of anti-CD34/PerCP-Cy5.5.

EXAMPLE 6

This Example illustrates the stability of formulations having various concentrations of a labeled binding agent and unconjugated PerCP in accordance with an embodiment of the present disclosure.

The stability of an anti-MPO antibody conjugated to PerCP-Cy5.5 (i.e., anti-MPO/PerCP-Cy5.5) at elevated temperature was examined. Anti-MPO/PerCP-Cy5.5 was used to stain blood from four healthy donors. The anti-MPO/PerCP-Cy5.5 conjugate was tested at a concentration of 50 µg/mL and 12.5 µg/mL in the presence of 130 µg/mL of unconjugated PerCP (+PerCP) (PhycoPro™ (PB40) from Prozyme Inc., isolated from Dinophyceae sp.) or in the absence of unconjugated PerCP (−PerCP). Prior to use, the reagent was stored at 4° C. or 37° C. for 3 days in a concentration of 50 µg/mL with or without unconjugated PerCP. For each sample, blood was stained using an intracellular staining procedure. For each sample, 50 µL blood was mixed with 100 µL IntraStain reagent A (DAKO) and fixed for 15 min at ambient temperature. EGTA was used as an anticoagulant. 2 mL PBS was added and cells were spun down at 300×g for 5 min at ambient temperature. Supernatant was removed. The cells were resuspended and the plasma membrane permeabilized in 100 µL IntraStain reagent B (DAKO). Staining formulation was added and the cells were incubated for 15 min at ambient temperature in the dark. 2 mL PBS was added, cells were spun down, resuspended in 0.4 mL PBS, and analyzed on a Navios Flow Cytometer (Beckmann Coulter). The cells were co-stained with CD45/Pacific Blue (DAKO) and granulocytes were gated on side scatter/Pacific blue plots.

The experimental histograms of granulocytes are shown in FIGS. 7A-8H, where signals from the experiments for formulations at 4° C. and 37° C. are overlayed. A four donor samples exhibited a decrease in median fluorescence intensity for the MPO positive cells stained with a formulation having no unconjugated PerCP. In contrast, cells stained with anti-MPO/PerCP-Cy5.5 in the presence of unconjugated PerCP provided similar histograms for formulations stored at 4° C. and 37° C. The results demonstrate that unconjugated PerCP increases the stability of anti-MPO/PerCP-Cy5.5.

EXAMPLE 7

This Example describes a procedure for using unconjugated PerCP fragments or variants thereof in accordance with an embodiment of the present disclosure.

Naturally-occurring variants and fragments of PerCP can be isolated from extracts of various organisms including Zooxanthellae (*Tridacna* species), *Amphidinium carterae* (Plymouth 450), *Cachonina niei, Gonyaulax polyedra, Glenodinium* species, *Amphidinium rhynocephaleium,* and *Gymnodinium splendens.* For example, PerCP complexes having variable amino acid sequences can be found in dinaflagellates such as *Amphidinium carterae.* PerCP variants may also be produced using an in vitro reconstitution system, as described in Schulte et al. (Eur. J. Cell Biol. 2010, 89, 990-997), which hereby incorporated by reference. In some embodiments, fragments of PerCP may be made using chemical or enzymatic methods for protein modifications (e.g. proteolytic modification of PerCP protein). In some embodiments, fragments or variants of PerCP may be made by using standard genetic engineering techniques to change the PerCP DNA sequences to code for fragments or variants of the PerCP protein. For example, in some embodiments, a modified sequence encoding expression of fragments or variants of PerCP may be made using in vitro synthesis, for example chemical DNA synthesis or enzyme mediated DNA synthesis. Sequences coding for fragments of PerCP may be made enzymatically by using amplification primers selected to generate the desired fragment. In some embodiments, mutagenesis or amplification with primers containing desired mutations may be used to generate variant proteins. In some embodiments, fragments or variants of PerCP may be made using non-algae host for recombinant expression such as *E. coli* as described by Miller et al. (Photosynthesis Research, 2005, 86, 229-240), which is hereby incorporated by reference. In some embodiments, fragments or variants of PerCP may be made by using standard genetic engineering techniques. The effects of the PerCP fragment or variant on the stability of a binding agent may be assessed using any of the methods described herein.

A formulation can be formed by combining one or more labeled binding agents comprising a binding moiety and a conjugated fluorochrome, and an unconjugated PerCP fragment or variant. For example, an anti-CD19/PerCP-Cy5.5 can be combined with an unconjugated PerCP fragment or variant. The PerCP fragment or variant may be used at any suitable concentration. For example, the formulation may comprise a PerCP fragment or variant at a concentration of from about 25 µg/mL to 150 µg/mL. The formulation may be used immediately after formation or stored for an extended period of time. For example, the formulation may be stored for up to 180 days. The formulation may be stored at any suitable temperature prior to use. For example, the formulation may be stored at a temperature of greater than about 4° C. (e.g., about 4° C. to about 40° C.) prior to use.

The formulation comprising the unconjugated PerCP fragment or variant and one or more labeled binding agents may be used in any suitable analytical process. For example, the formulation may be used in a flow cytometry method. In such cases, the sample comprising one or more cells is contacted with the formulation comprising the unconjugated PerCP fragment or variant and one or more labeled binding agents. The analytical sample is analyzed using flow cytometry. For example, a cell suspension is contacted with the formulation comprising the unconjugated PerCP fragment or variant and one or more labeled binding agents, followed by staining of the cells. A lysing solution may be added to the analytical sample, and the analytical sample may be incubated. The analytical sample can be run on a flow cytometer, generating histograms that provide information or data relating to one or more parameters of the cell(s).

EXAMPLE 8

This Example illustrates the stability of formulations having various concentrations of a labeled binding agent and unconjugated PerCP in accordance with an embodiment of the present disclosure.

Figure 9:
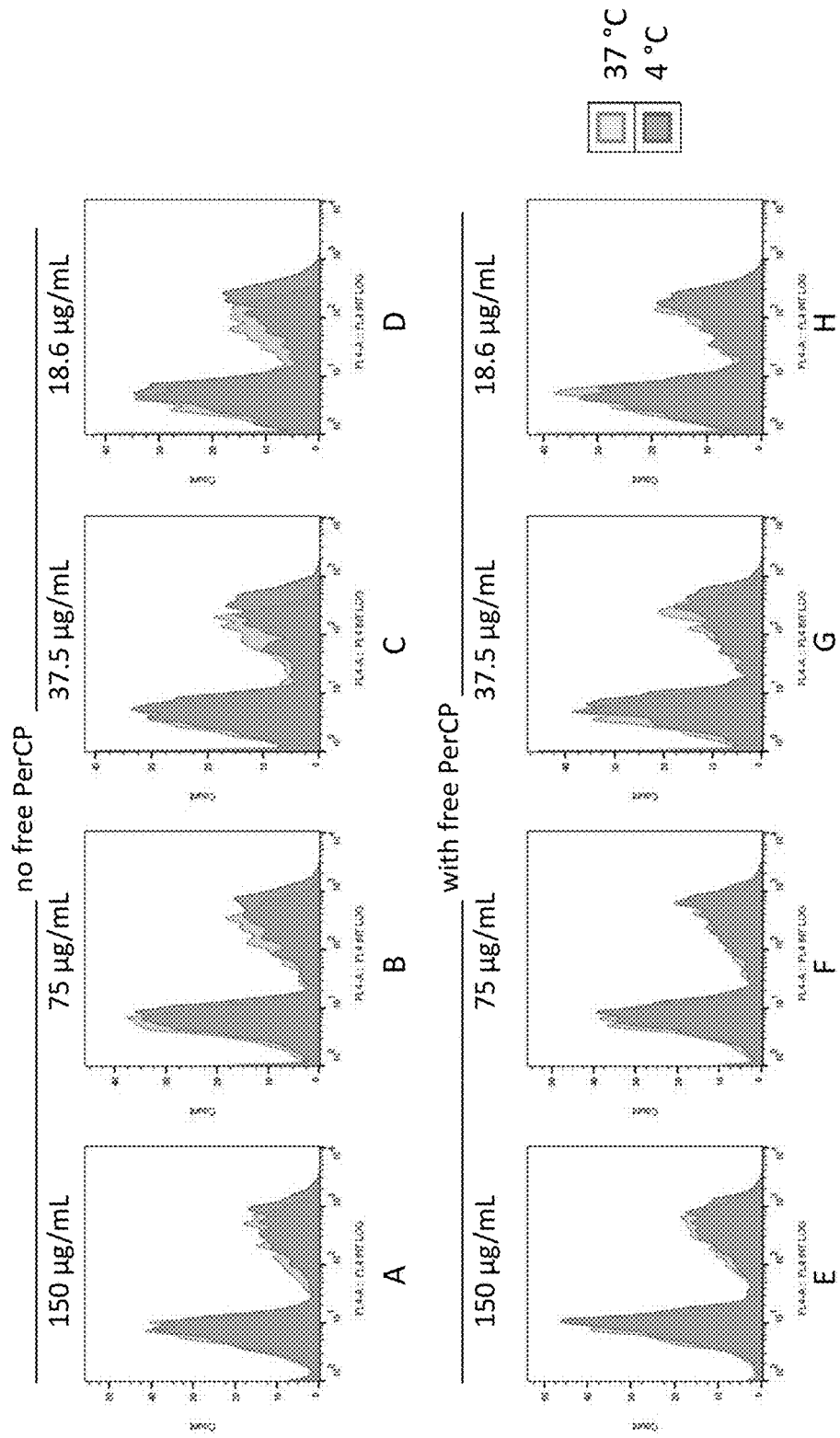
FIGS. 9A-9H are histograms showing flow cytometry data for stability testing of formulations comprising polyclonal F(ab')2 rabbit Anti-Human Lambda Light Chains/PerCP-Cy5.5 which comprises polyclonal F(ab')2 rabbit Anti-Human Lambda Light Chains conjugated with the fluorochrome PerCP-Cy5.5 in the absence and presence of unconjugated PerCP. The polyclonal F(ab')2 rabbit Anti-Human Lambda Light Chains/PerCP-Cy5.5 conjugate was tested at concentrations of 150 µg/mL (FIGS. 9A and 9E), 75 µg/mL (FIGS. 9B and 9F), 37.5 µg/mL (FIGS. 9C and 9G) and 18.6 µg/mL (FIGS. 9D and 9H). The polyclonal F(ab')2 rabbit Anti-Human Lambda Light Chains/PerCP-Cy5.5 conjugate was tested with no free PerCP (FIGS. 9A-9D) and with 90 µg/mL free PerCP (FIGS. 9E-9H). The polyclonal F(ab')2 rabbit Anti-Human Lambda Light Chains/PerCP-Cy5.5 conjugate was incubated 3 days at 37° C. (light grey) and compared to a reference stored at 4° C. (dark grey).

Blood was stained with polyclonal F(ab')2 rabbit Anti-Human Lambda Light Chains/PerCP-Cy5.5 in varying concentrations and CD19/FITC reagent. Lymphocytes were first gated on forward/sidescatter dot plots. B-cells were gated as CD19 positive lymphocytes on FITC/sidescatter dot plots. FIG. 9 depicts PerCP-Cy5.5 histograms of B-cells.

FIGS. 9A-9H are histograms showing flow cytometry data for stability testing of formulations comprising polyclonal F(ab')2 rabbit Anti-Human Lambda Light Chains/PerCP-Cy5.5 which comprises polyclonal F(ab')2 rabbit Anti-Human Lambda Light Chains conjugated with the fluorochrome PerCP-Cy5.5 in the absence and presence of unconjugated PerCP. The polyclonal F(ab')2 rabbit Anti-Human Lambda Light Chains/PerCP-Cy5.5 conjugate was tested at concentrations of 150 µg/mL (FIGS. 9A and 9E), 75 µg/mL (FIGS. 9B and 9F), 37.5 µg/mL (FIGS. 9C and 9G) and 18.6 µg/mL (FIGS. 9D and 9H). The polyclonal F(ab')2 rabbit Anti-Human Lambda Light Chains/PerCP-Cy5.5 conjugate was tested with no free PerCP (FIGS. 9A-D) and with 90 µg/mL free PerCP (FIGS. 9E-9H). The polyclonal F(ab')2 rabbit Anti-Human Lambda Light Chains/PerCP-Cy5.5 conjugates were incubated 3 days at 37° C. (light grey) and compared to a referenced stored at 4° C. (dark grey). Stability of reagent with 90 µg/mL free PerCP added (FIGS. 9E-9H) is higher at 37° C. than reagent without addition of free PerCP (FIGS. 9A-9D).

EXAMPLE 9

This Example illustrates the stability of formulations having various concentrations of a labeled binding agent and unconjugated PerCP in accordance with an embodiment of the present disclosure.

Figure 10:
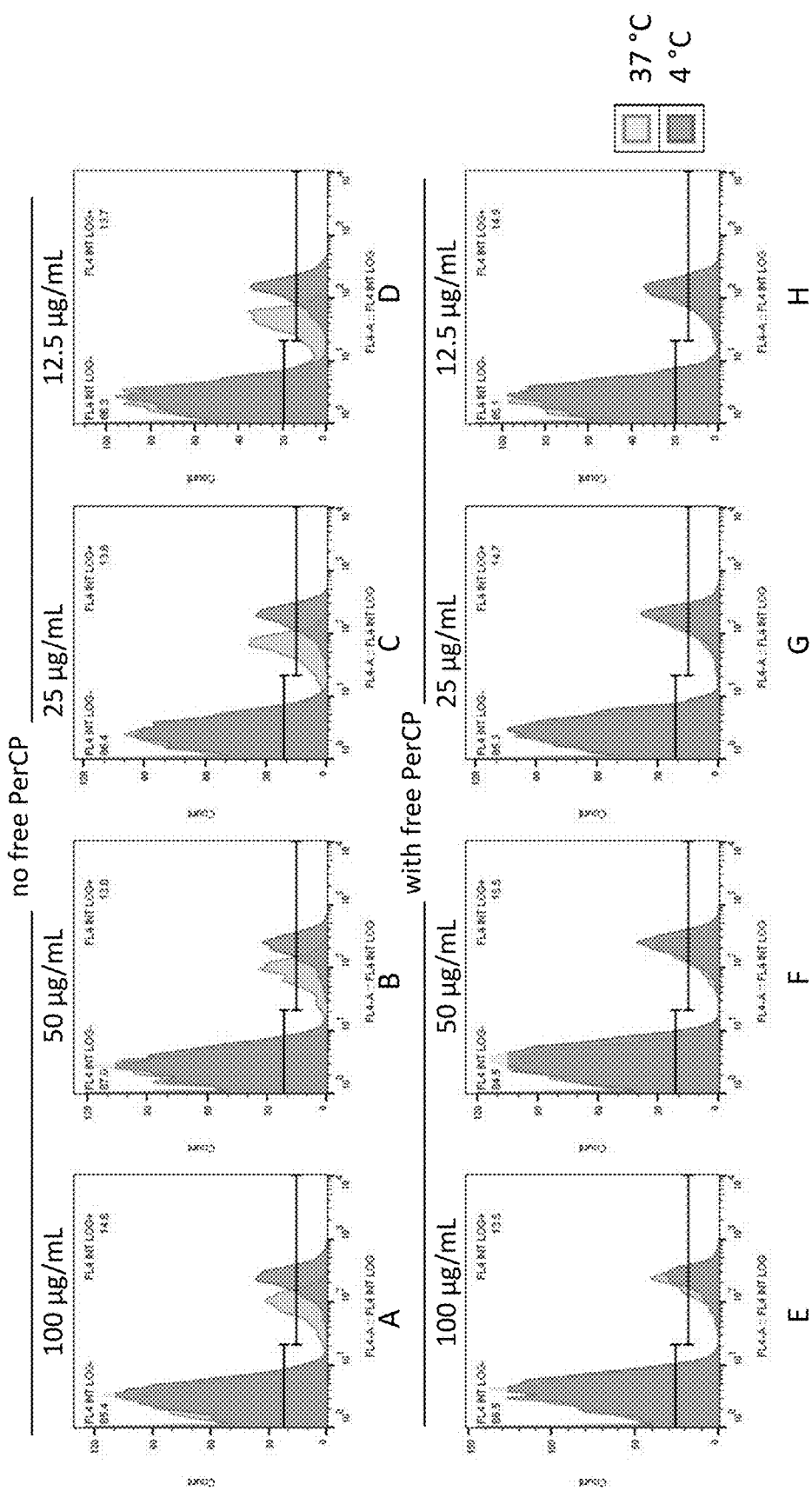
FIGS. 10A-10H are histograms showing flow cytometry data for stability testing of formulations comprising mouse monoclonal Anti-Human CD22/PerCP-Cy5.5 (isotype IgG1 kappa) which comprises mouse monoclonal Anti-Human CD22 conjugated with the fluorochrome PerCP-Cy5.5 in the absence and presence of unconjugated PerCP. The mouse monoclonal Anti-Human CD22/PerCP-Cy5.5 conjugate was tested at concentrations of 100 µg/mL (FIGS. 10A and 10E), 50 µg/mL (FIGS. 10B and 10F), 25 µg/mL (FIGS. 10C and 10G), and 12.5 µg/mL (FIGS. 10D and 10H). The mouse monoclonal Anti-Human CD22/PerCP-Cy5.5 conjugate was tested with no free PerCP (FIGS. 10A-10D) and with 130 µg/mL free PerCP (FIGS. 10E-10H). The mouse monoclonal Anti-Human CD22/PerCP-Cy5.5 conjugate was incubated 3 days at 37° C. (light grey) and compared to a reference stored at 4° C. (dark grey).

Blood was stained with mouse monoclonal Anti-Human CD22/PerCP-Cy5.5 (isotype IgG1 kappa) reagent in varying concentrations. Lymphocytes were gated on forward/sidescatter dot plots. FIG. 10 includes PerCP-Cy5.5 histograms of lymphocytes obtained with blood stained with mouse monoclonal Anti-Human CD22/PerCP-Cy5.5 (isotype IgG1 kappa), either a 4° C. reference (dark grey) or reagent stored at 37° C. for three days (light grey). Reagent was without addition of free PerCP (FIGS. 10A-10D) or contained 130 µg/mL free PerCP (FIGS. 10E-10H).

FIGS. 10A-10H are histograms showing flow cytometry data for stability testing of formulations comprising mouse monoclonal Anti-Human CD22/PerCP-Cy5.5 (isotype IgG1 kappa) which comprises mouse monoclonal Anti-Human CD22 conjugated with the fluorochrome PerCP-Cy5.5 in the absence and presence of unconjugated PerCP. The mouse monoclonal Anti-Human CD22/PerCP-Cy5.5 conjugate was tested at concentrations of 100 µg/mL (FIGS. 10A and 10E), 50 µg/mL (FIGS. 10B and 10F), 25 µg/mL (FIGS. 10C and 10G), and 12.5 µg/mL (FIGS. 10D and 10H). The mouse monoclonal Anti-Human CD22/PerCP-Cy5.5 conjugate was tested with no free PerCP (FIGS. 10A-10D) and with 1300 µg/mL free PerCP (FIGS. 10E-10H). The mouse monoclonal Anti-Human CD22/PerCP-Cy5.5 conjugate was incubated 3 days at 37° C. (light grey) and compared to a reference stored at 4° C. (dark grey). Stability of reagent with 130 µg/mL free PerCP added (FIGS. 10E-10H) is higher at 37° C. than reagent without addition of free PerCP (FIGS. 10A-10D).

EXAMPLE 10

This Example illustrates the stability of formulations having various concentrations of a labeled binding agent and unconjugated PerCP in accordance with an embodiment of the present disclosure.

A mix of HPB-ALL (CD1a positive) and Daudi (CD1a negative) cells were stained with mouse monoclonal Anti-Human CD1a/PerCP-Cy5.5 in varying concentrations. Cells were gated on forward scatter/side scatter dot plots and further gated as singlets on sidescatter (H)/sidescatter (A) plots. Prior to staining procedure, reagent was stored for 3 days at 37° C. (light grey) with reference reagent stored at 4° C. (dark grey). Reagent was without addition of free PerCP (FIGS. 11A-11D) or contained 130 µg/mL free PerCP (FIGS. 11E-11H).

Figure 11:
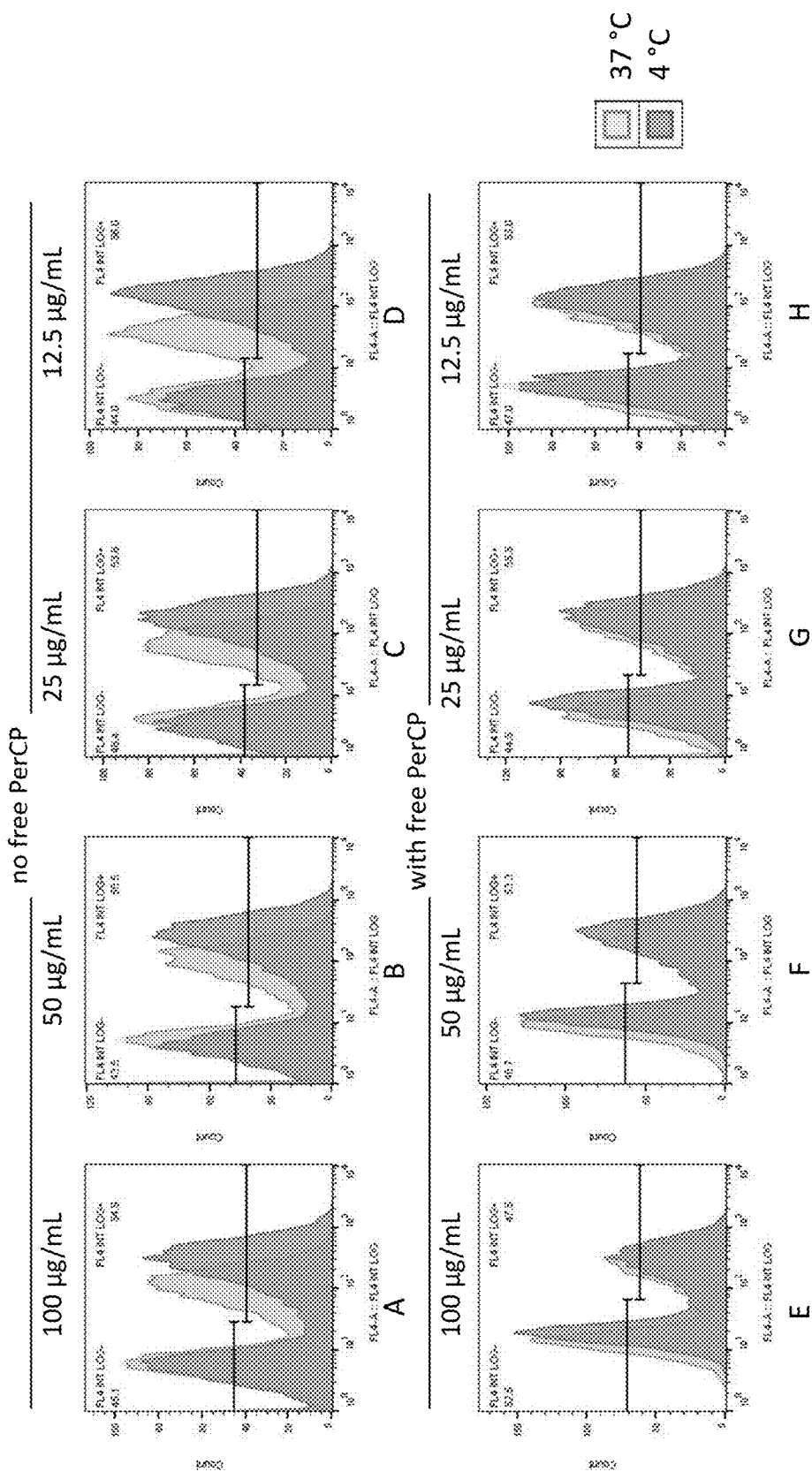
FIGS. 11A-11H are histograms showing flow cytometry data for stability testing of formulations comprising mouse monoclonal Anti-Human CD1a/PerCP-Cy5.5 (isotype: IgG2a kappa) which comprises mouse monoclonal Anti-Human CD1a conjugated with the fluorochrome PerCP-Cy5.5 in the absence and presence of unconjugated PerCP. The mouse monoclonal Anti-Human CD1a/PerCP-Cy5.5 conjugate was tested at concentrations of 100 µg/mL (FIGS. 11A and 11E), 50 µg/mL (FIGS. 11B and 11F), 25 µg/mL (FIGS. 11C and 11G), and 12.5 µg/mL (FIGS. 11D and 11H). The mouse monoclonal Anti-Human CD1a/PerCP-Cy5.5 conjugate was tested with no free PerCP (FIGS. 11A-11D) and with 130 µg/mL free PerCP (FIGS. 11E-11H). The mouse monoclonal Anti-Human CD1a/PerCP-Cy5.5 conjugate was incubated 3 days at 37° C. (light grey) and compared to a reference stored at 4° C. (dark grey).

FIGS. 11A-11H are histograms showing flow cytometry data for stability testing of formulations comprising mouse monoclonal Anti-Human CD1a/PerCP-Cy5.5 (isotype: IgG2a kappa) which comprises mouse monoclonal Anti-Human CD1a conjugated with the fluorochrome PerCP-Cy5.5 in the absence and presence of unconjugated PerCP. The mouse monoclonal Anti-Human CD1a/PerCP-Cy5.5 conjugate was tested at concentrations of 100 µg/mL (FIGS. 11A and 11E), 50 µg/mL (FIGS. 11B and 11F), 25 µg/mL (FIGS. 11C and 11G), and 12.5 µg/mL (FIGS. 11D and 11H). The mouse monoclonal Anti-Human CD1a/PerCP-Cy5.5 conjugate was tested with no free PerCP (FIGS. 11A-11D) and with 130 µg/mL free PerCP (FIGS. 11E-11H). The mouse monoclonal Anti-Human CD1a/PerCP-Cy5.5 conjugate was incubated 3 days at 37° C. (light grey) and compared to a reference stored at 4° C. (dark grey). Stability of reagent with 130 µg/mL free PerCP added (FIGS. 11E-11H) is higher at 37° C. than reagent without addition of free PerCP (FIGS. 11A-11D).

EXAMPLE 11

This Example illustrates the stability of formulations having various concentrations of a labeled binding agent and unconjugated PerCP in accordance with an embodiment of the present disclosure.

Figure 12:
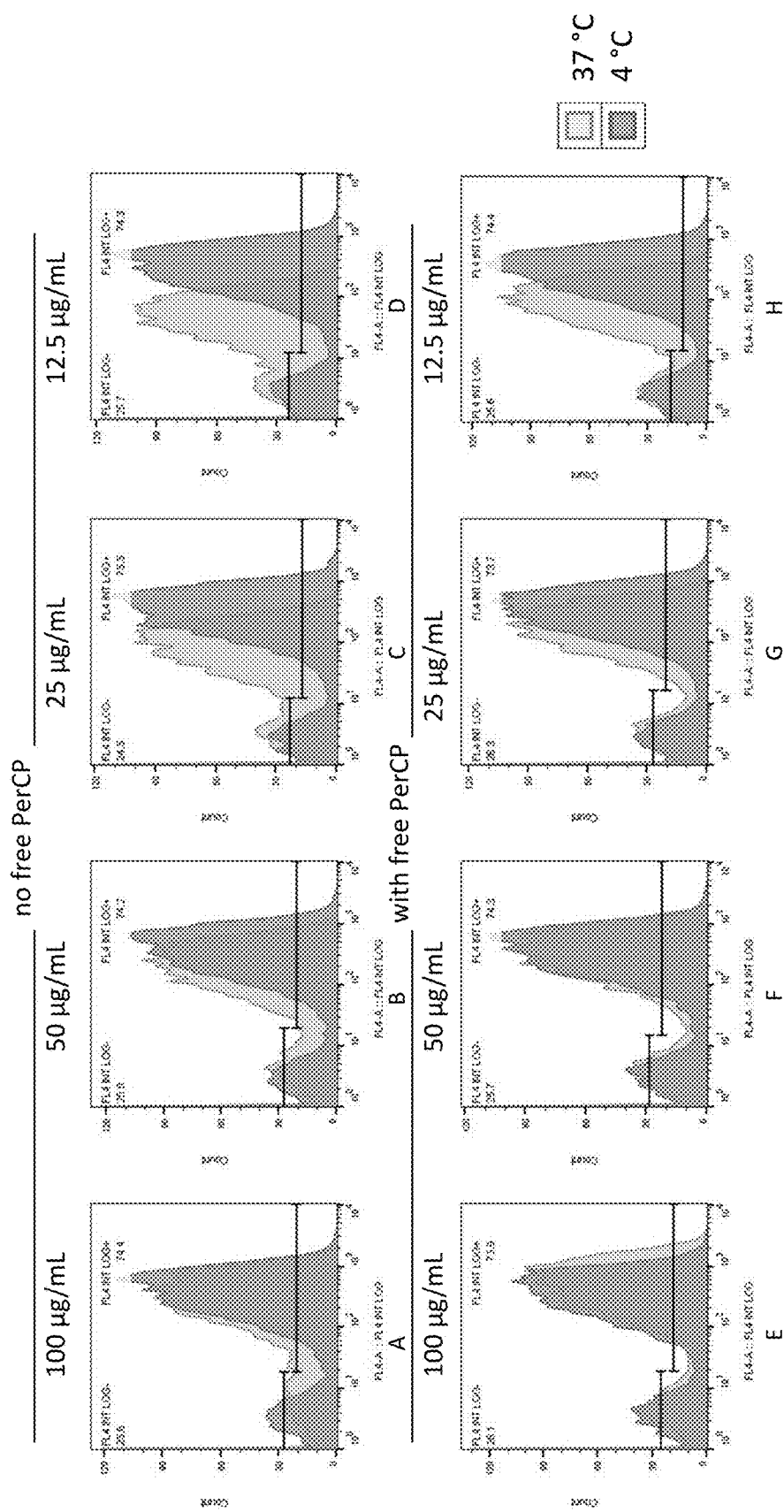
FIGS. 12A-12H are histograms showing flow cytometry data for stability testing of formulations comprising mouse monoclonal Anti-Human CD7/PerCP-Cy5.5 (isotype: IgG2b kappa) which comprises mouse monoclonal Anti-Human CD7 conjugated with the fluorochrome PerCP-Cy5.5 in the absence and presence of unconjugated PerCP. The mouse monoclonal Anti-Human CD7/PerCP-Cy5.5 conjugate was tested at concentrations of 100 µg/mL (FIGS. 12A and 12E), 50 µg/mL (FIGS. 12B and 12F), 25 µg/mL (FIGS. 12C and 12G), and 12.5 µg/mL (FIGS. 12D and 12H). The mouse monoclonal Anti-Human CD7/PerCP-Cy5.5 conjugate was tested with no free PerCP (FIGS. 12A-12D) and with 130 µg/mL free PerCP (FIGS. 12E-12H). The mouse monoclonal Anti-Human CD7/PerCP-Cy5.5 conjugate was incubated 3 days at 37° C. (light grey) and compared to a reference stored at 4° C. (dark grey).

Blood was stained with mouse monoclonal Anti-Human CD7/PerCP-Cy5.5 reagent in varying concentrations. Lymphocytes were gated on forward/sidescatter dot plots. FIG. 12 includes PerCP-Cy5.5 histograms of lymphocytes stained with mouse monoclonal Anti-Human CD7/PerCP-Cy5.5, either a 4° C. reference (dark grey) or reagent stored at 37° C. for three days (light grey). Reagent was without addition of free PerCP (FIGS. 12A-12D) or contained 130 µg/mL free PerCP (FIGS. 12E-12H).

FIGS. 12A-12H are histograms showing flow cytometry data for stability testing of formulations comprising mouse monoclonal Anti-Human CD7/PerCP-Cy5.5 (isotype:

IgG2b kappa) which comprises mouse monoclonal Anti-Human CD7 conjugated with the fluorochrome PerCP-Cy5.5 in the absence and presence of unconjugated PerCP. The mouse monoclonal Anti-Human CD7/PerCP-Cy5.5 conjugate was tested at concentrations of 100 μg/mL (FIGS. 12A and 12E), 50 μg/mL (FIGS. 12B and 12F), 25 μg/mL (FIGS. 12C and 12G), and 12.5 μg/mL (FIGS. 12D and 12H). The mouse monoclonal Anti-Human CD7/PerCP-Cy5.5 conjugate was tested with no free PerCP (FIGS. 12A-12D) and with 130 μg/mL free PerCP (FIGS. 12E-12H). The mouse monoclonal Anti-Human CD7/PerCP-Cy5.5 conjugate was incubated 3 days at 37° C. (light grey) and compared to a reference stored at 4° C. (dark grey). Stability of reagent with 130 μg/mL free PerCP added (FIGS. 11E-11H) is higher at 37° C. than reagent without addition of free PerCP (FIGS. 11A-11D).

We claim:

1. A stable formulation comprising (a) at least one labeled binding agent comprising a binding moiety and a conjugated PerCP fluorochrome, and (b) at least one unconjugated peridinin chlorophyll protein complex (PerCP), wherein the formulation has a total PerCP concentration of at least about 0.1 μg/mL.

2. The formulation of claim 1, wherein the conjugated PerCP fluorochrome is a PerCP tandem fluorochrome.

3. The formulation of claim 2, wherein the PerCP tandem fluorochrome is peridinin chlorophyll protein-cyanine 5.5.

4. The formulation of claim 1, wherein the unconjugated PerCP is at a concentration of at least about 50 μg/mL.

5. The formulation of claim 1, wherein the labeled binding agent comprises an anti-CD19 antibody, an anti-CD34 antibody, or an anti-MPO antibody.

6. The formulation of claim 1, wherein the ratio of the unconjugated PerCP to the labeled binding agent is at least about 2:1.

7. The formulation of claim 1, wherein the unconjugated PerCP is a full-length PerCP.

8. The formulation of claim 1, wherein the unconjugated PerCP is a peridinin chlorophyll protein complex that is not attached or bound to another chemical moiety.

9. The formulation of claim 1, wherein the formulation has greater stability than a formulation having no unconjugated PerCP.

10. The formulation of claim 1, wherein the fluorescence intensity of the formulation changes by about 25% or less at a temperature of about 20° C. for from about 1 day to about 180 days.

11. The formulation of claim 1, wherein the labeled binding agent in the presence of unconjugated PerCP has a change in fluorescence intensity of about 25% or less when the temperature of the formulation is increased from about 4° C. by at least about 10° C. for 35-150 days.

12. A method of analyzing a sample using flow cytometry, the method comprising: contacting a sample comprising cells with the formulation of claim 1 to form an analytical sample, and analyzing the analytical sample using flow cytometry;
wherein the formulation has a total peridinin chlorophyll protein complex (PerCP) concentration of at least about 0.1 μg/mL.

13. The method of claim 12, wherein the conjugated PerCP fluorochrome is a PerCP tandem fluorochrome.

14. The method of claim 13, wherein the PerCP tandem fluorochrome is peridinin chlorophyll protein-cyanine 5.5.

15. The method of claim 12, wherein the formulation has a total concentration of PerCP of at least about 75 μg/mL.

16. The method of claim 12, wherein the method further comprises sorting cells in the cell composition based on fluorescence emission of the fluorochrome.

17. The method of claim 12, wherein the labeled binding agent comprises an anti-CD19 antibody, an anti-CD34 antibody, or an anti-MPO antibody.

18. The method of claim 12, wherein the cells are human blood cells.

19. The method of claim 12, wherein the contacting is performed at a temperature of at least about 20° C.

20. A kit comprising (a) at least one labeled binding agent comprising a binding moiety and a conjugated PerCP fluorochrome, and (b) at least one unconjugated PerCP.

21. The kit of claim 20, wherein the conjugated PerCP fluorochrome is peridinin chlorophyll protein-cyanine 5.5 and the kit is stored at a temperature of at least about 20° C.

* * * * *